United States Patent
Cho

(10) Patent No.: US 7,836,548 B2
(45) Date of Patent: Nov. 23, 2010

(54) VACUUM CLEANER

(75) Inventor: Young-Man Cho, Yongin-si (KR)

(73) Assignee: Bukang Sems Co., Ltd. (KR)

( * ) Notice: Subject to any disclaimer, the term of this patent is extended or adjusted under 35 U.S.C. 154(b) by 40 days.

(21) Appl. No.: 11/934,563

(22) Filed: Nov. 2, 2007

(65) Prior Publication Data

US 2008/0052872 A1    Mar. 6, 2008

Related U.S. Application Data

(63) Continuation of application No. PCT/KR2006/001745, filed on May 10, 2006.

(30) Foreign Application Priority Data

| May 12, 2005 | (KR) | .................... 10-2005-0039553 |
| Sep. 22, 2005 | (KR) | .................... 10-2005-0087990 |

(51) Int. Cl.
*A47L 9/08* (2006.01)
(52) U.S. Cl. .................... 15/421; 15/382; 15/347
(58) Field of Classification Search .................... 15/339, 15/382, 347, 421; 134/21
See application file for complete search history.

(56) References Cited

U.S. PATENT DOCUMENTS

| 1,792,992 | A | | 2/1931 | Lerch |
| 2,581,794 | A | * | 1/1952 | Hodges .................... 15/364 |
| 2,590,152 | A | | 3/1952 | Buckey |
| 3,975,790 | A | | 8/1976 | Patterson |
| 4,907,316 | A | | 3/1990 | Kurz |
| 5,218,376 | A | | 6/1993 | Asai |
| 5,233,723 | A | * | 8/1993 | Hung .................... 15/339 |
| 5,901,411 | A | | 5/1999 | Hato et al. |
| 6,776,824 | B2 | * | 8/2004 | Wen .................... 96/223 |
| 7,251,853 | B2 | * | 8/2007 | Park et al. .................... 15/319 |
| 7,444,711 | B2 | * | 11/2008 | Garcia et al. .................... 15/324 |
| 7,476,885 | B2 | * | 1/2009 | Garcia et al. .................... 250/504 H |
| 2005/0050670 | A1 | * | 3/2005 | Kumazaki .................... 15/320 |
| 2006/0288517 | A1 | * | 12/2006 | Oh et al. .................... 15/320 |

FOREIGN PATENT DOCUMENTS

DE    41 39 199 A1    6/1993

(Continued)

OTHER PUBLICATIONS

European Search Report of Related European Patent Application No. 06768477.9 dated Mar. 10, 2009—14 Pages.

(Continued)

*Primary Examiner*—Dung Van Nguyen
(74) *Attorney, Agent, or Firm*—Knobbe Martens Olson & Bear LLP

(57) ABSTRACT

The sterilizing vacuum cleaner for bed clothes includes a housing including an ultraviolet (UV) irradiating space depressed into a bottom surface thereof, a suction port formed in the UV irradiating space, a discharge port formed in a side surface thereof, an air passage for connecting the suction port and the discharge port, and a sticking prevention passage depressed into the bottom extending to the side surface to prevent an object to be sterilized from adhering to the bottom surface. A first UV light emitter is installed in the housing to irradiate ultraviolet rays to the UV irradiating space of the housing.

17 Claims, 18 Drawing Sheets

FOREIGN PATENT DOCUMENTS

| | | |
|---|---|---|
| GB | 648967 | 1/1951 |
| JP | 55-159044 U | 11/1980 |
| JP | 01-308514 A | 12/1989 |
| JP | 02-243123 A | 9/1990 |
| JP | 03-182223 A | 8/1991 |
| JP | 03-284227 A | 12/1991 |
| JP | 04-089018 A | 3/1992 |
| JP | 04-156808 A | 5/1992 |
| JP | 08-131522 | 5/1996 |
| JP | 08-280779 | 10/1996 |
| JP | 09-084726 A | 3/1997 |
| JP | 09-182702 A | 7/1997 |
| JP | 2747357 B2 | 2/1998 |
| JP | 11-137483 A | 5/1999 |
| JP | 3104086 U | 9/2004 |
| KR | 1996-0003673 A | 2/1996 |
| KR | 1998-020751 U | 7/1998 |
| KR | 1999-019515 A | 3/1999 |
| KR | 20-0143204 Y1 | 6/1999 |
| KR | 1999-0068388 A | 9/1999 |
| KR | 10-2000-0072315 A | 12/2000 |
| KR | 20-0258304 Y1 | 12/2001 |
| KR | 20-0353596 Y1 | 6/2004 |
| KR | 20-0367735 Y1 | 11/2004 |
| KR | 1020040100409 A | 12/2004 |
| KR | 20-0382161 Y1 | 4/2005 |
| KR | 10-2006-0084175 A | 7/2006 |
| WO | 03/059492 A1 | 7/2003 |
| WO | 2006-015390 A2 | 2/2006 |

OTHER PUBLICATIONS

International Search Report dated Sep. 20, 2006 in PCT/KR2006/001745 in 3 pages.

Notification of Reasons for Rejection dated Nov. 10, 2009 of corresponding Japanese Patent Application No. 2008-511053—3 pages.

* cited by examiner

[Figure 1]
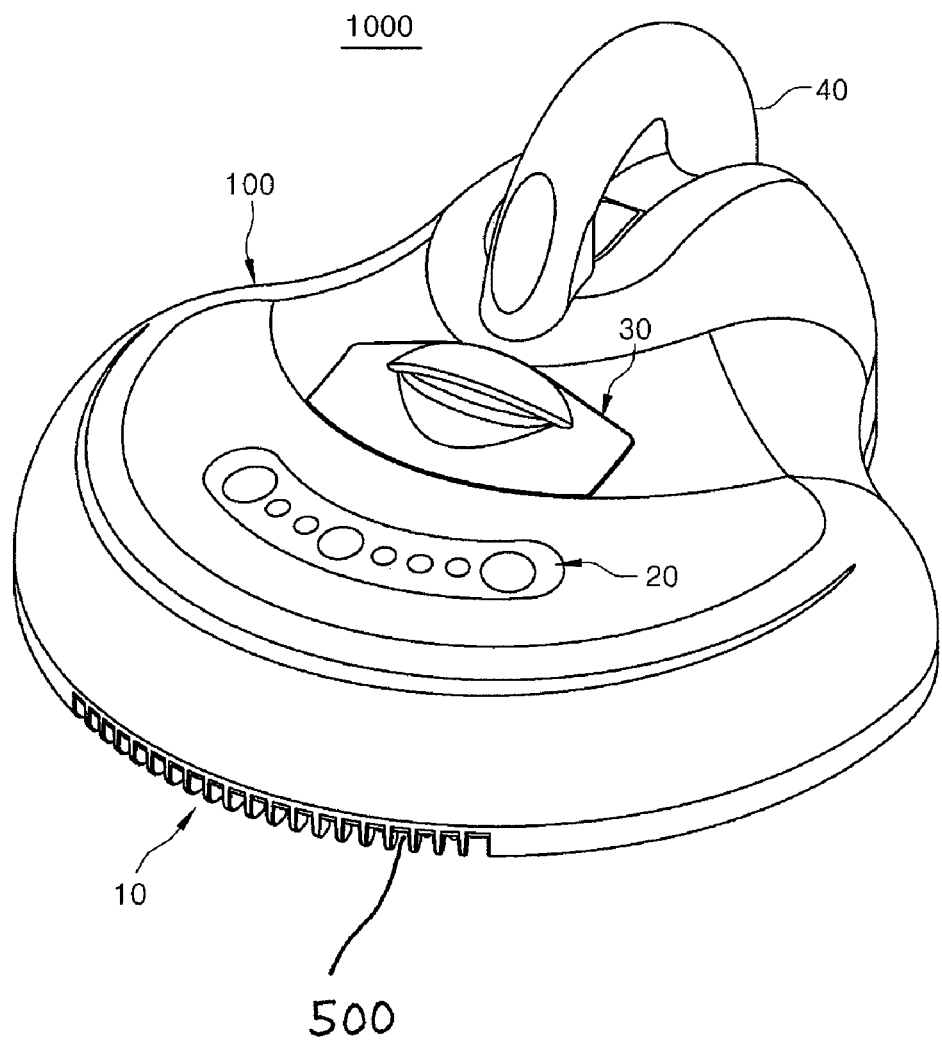

[Figure 2]
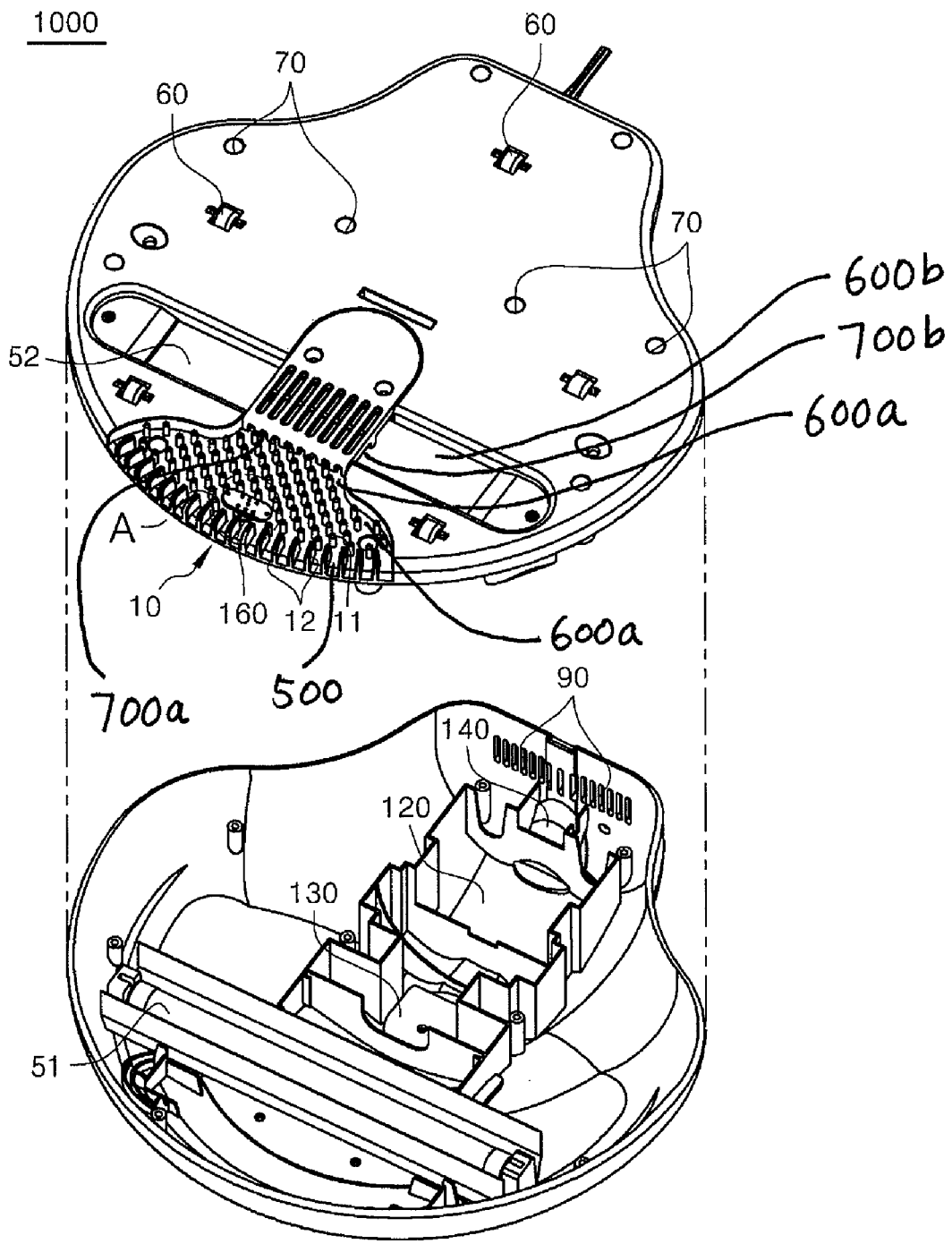

[Figure 3]
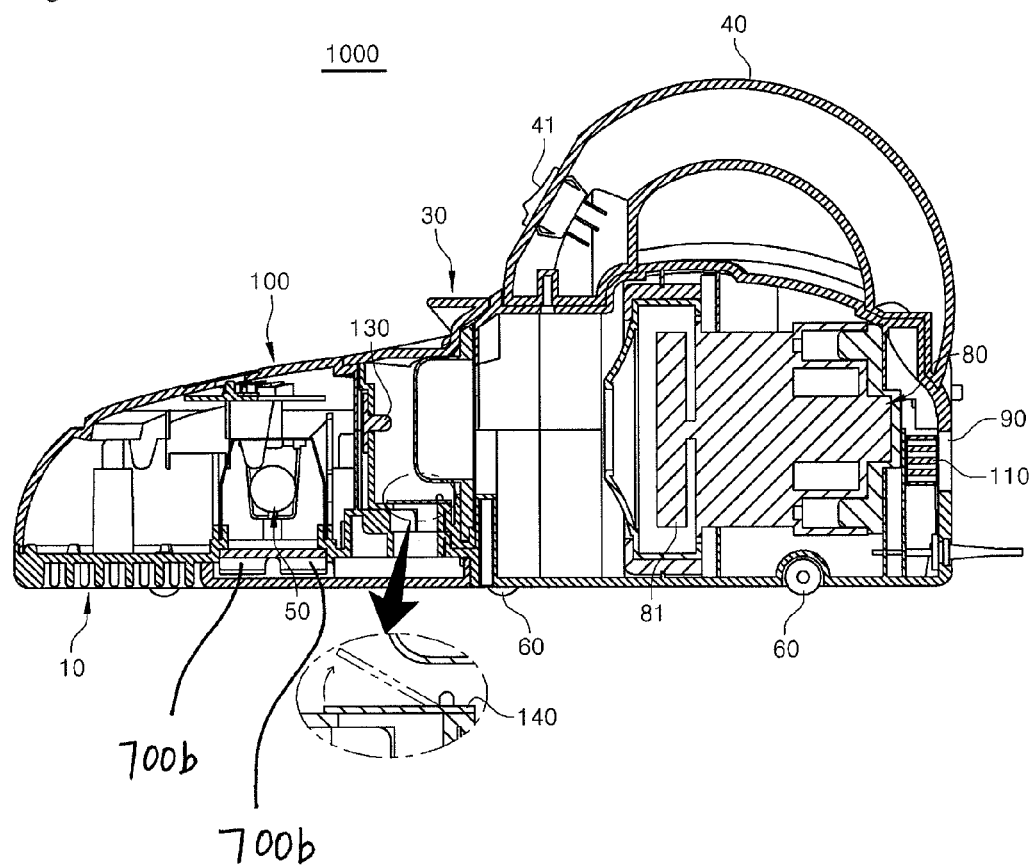

[Figure 4]
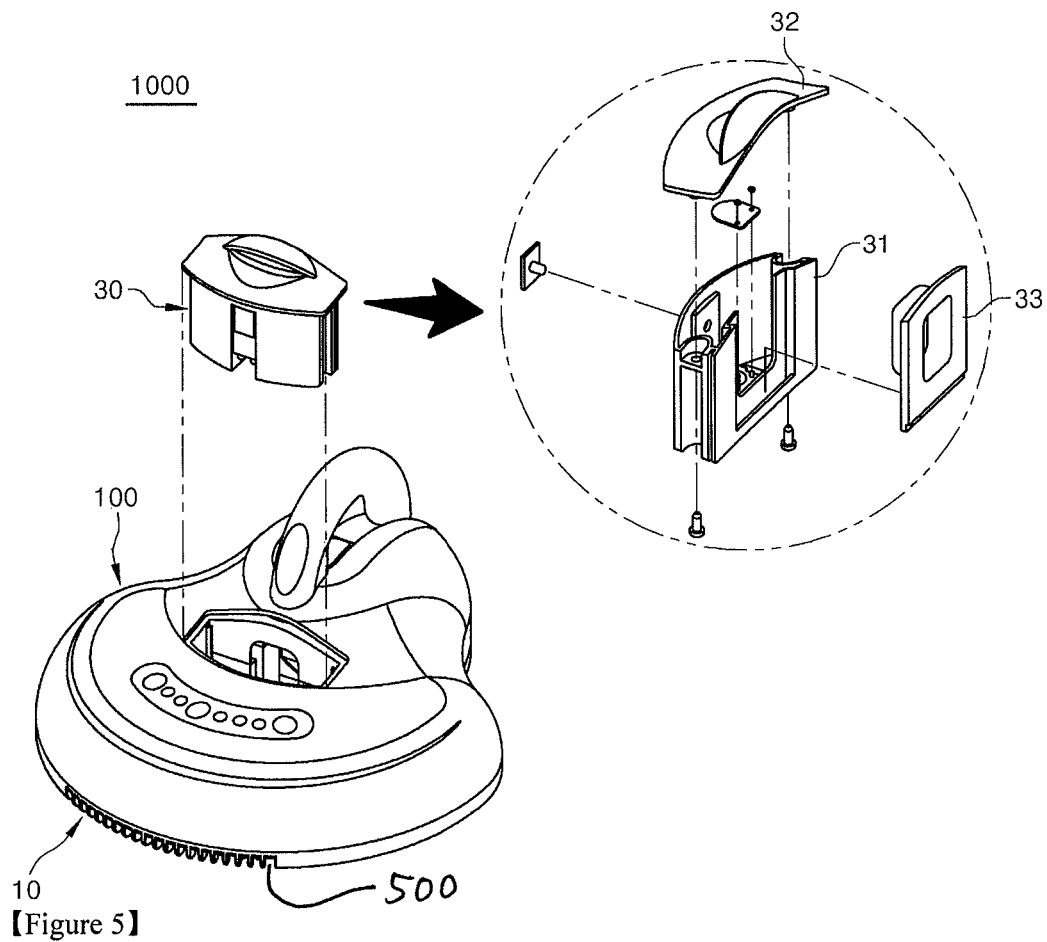
[Figure 5]
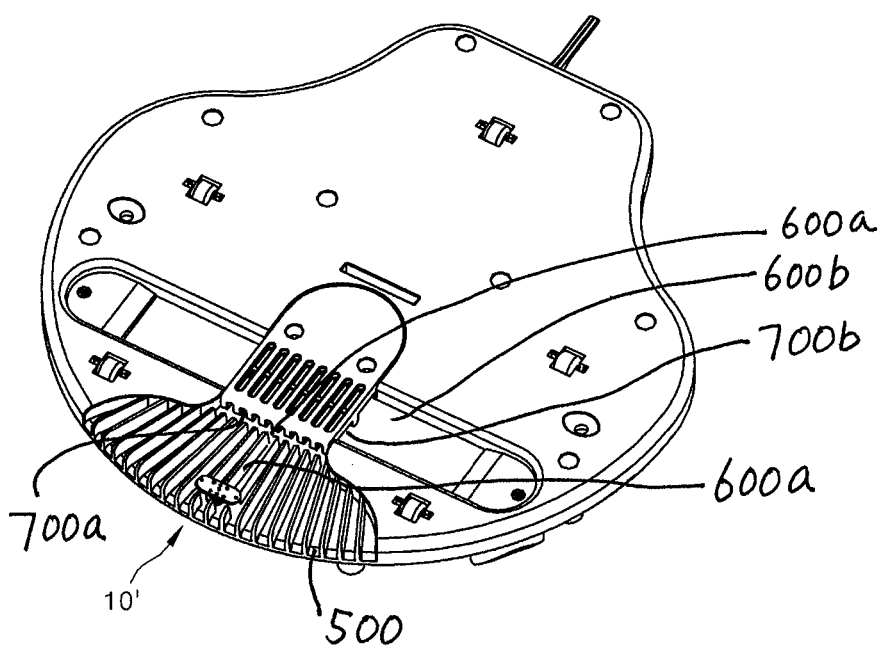

[Figure 6]
(a)
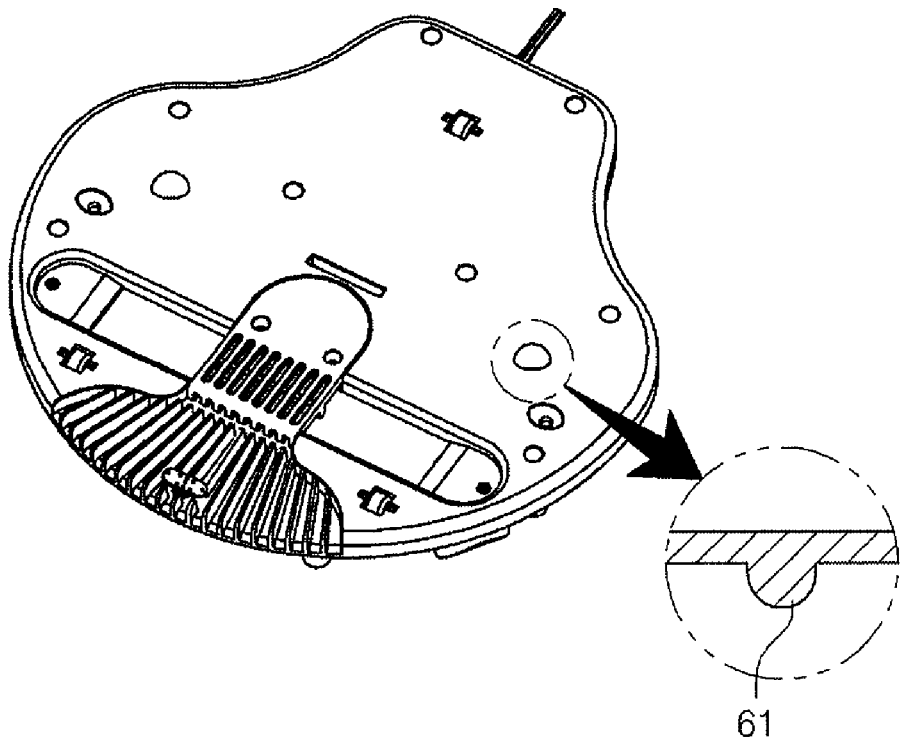
61
(b)
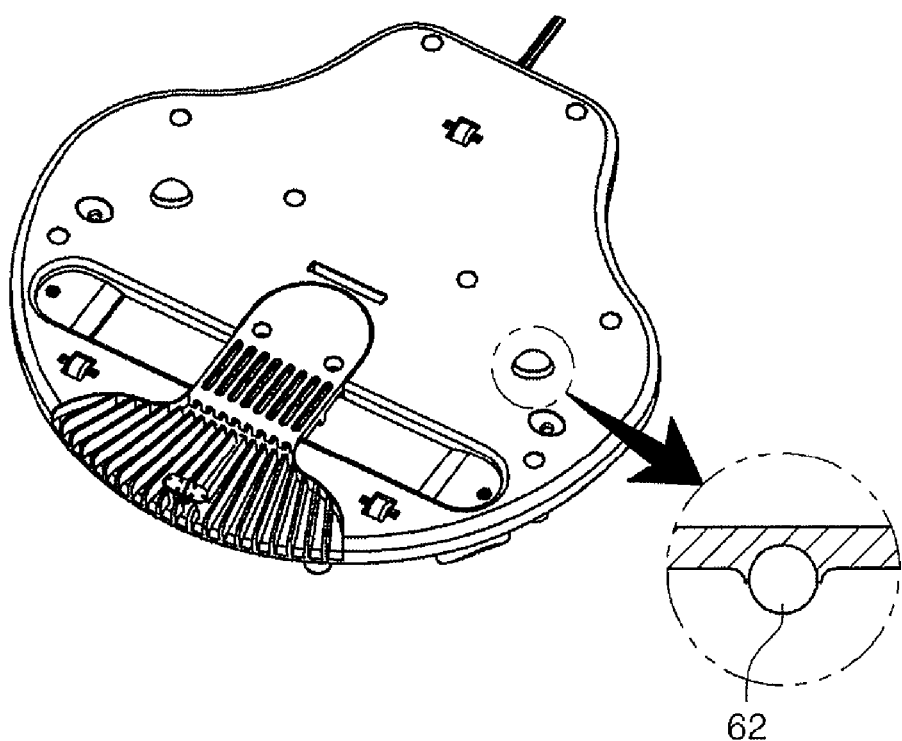
62

[Figure 7]
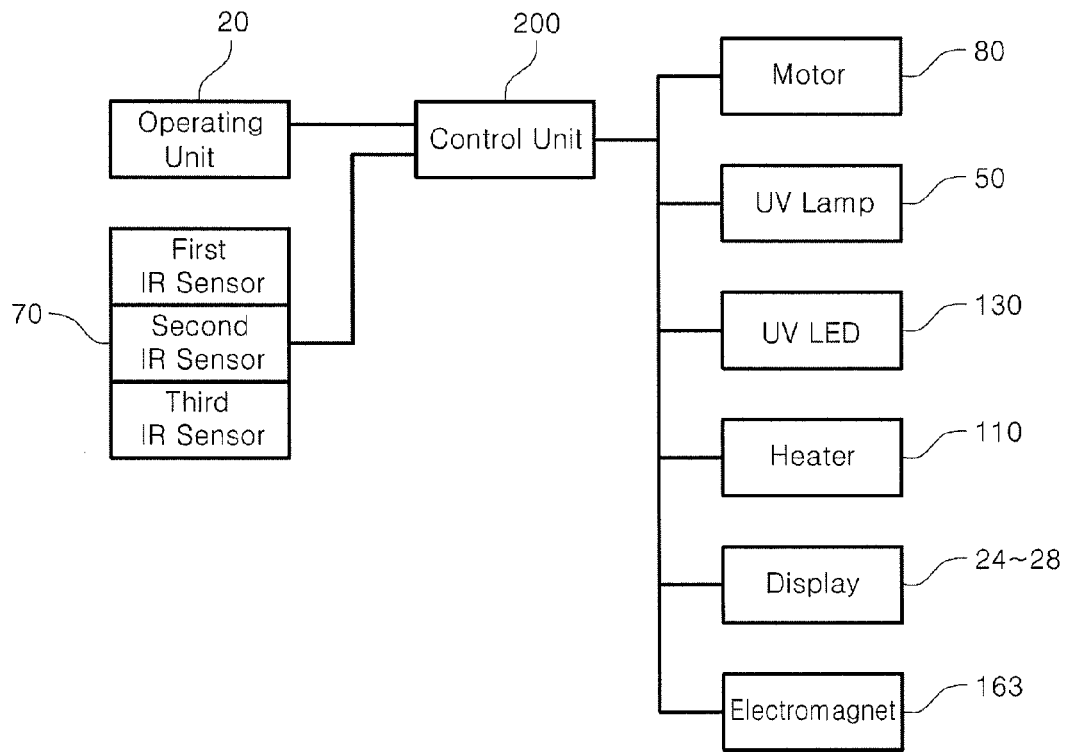
[Figure 8]
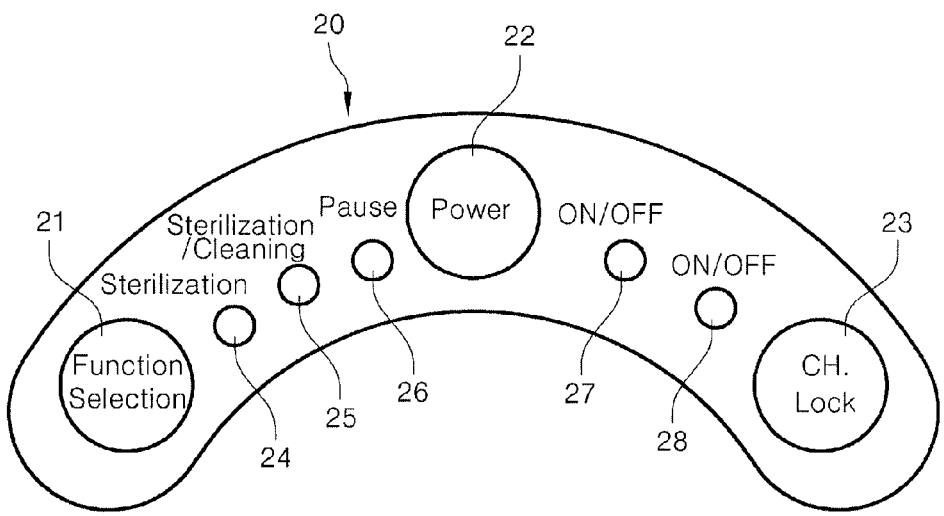

[Figure 9]
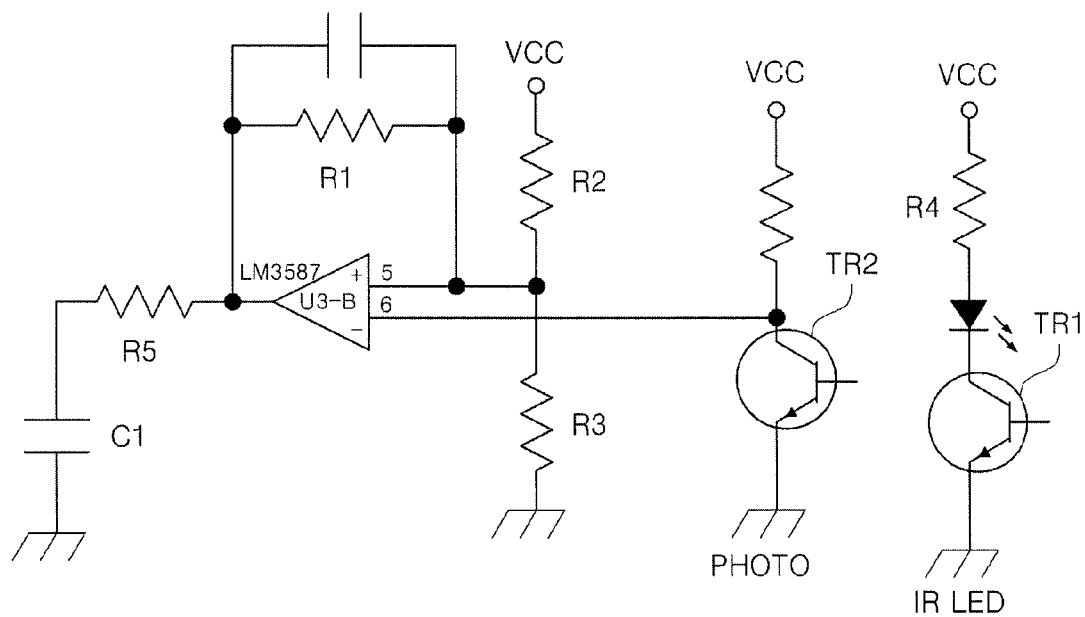

[Figure 10]
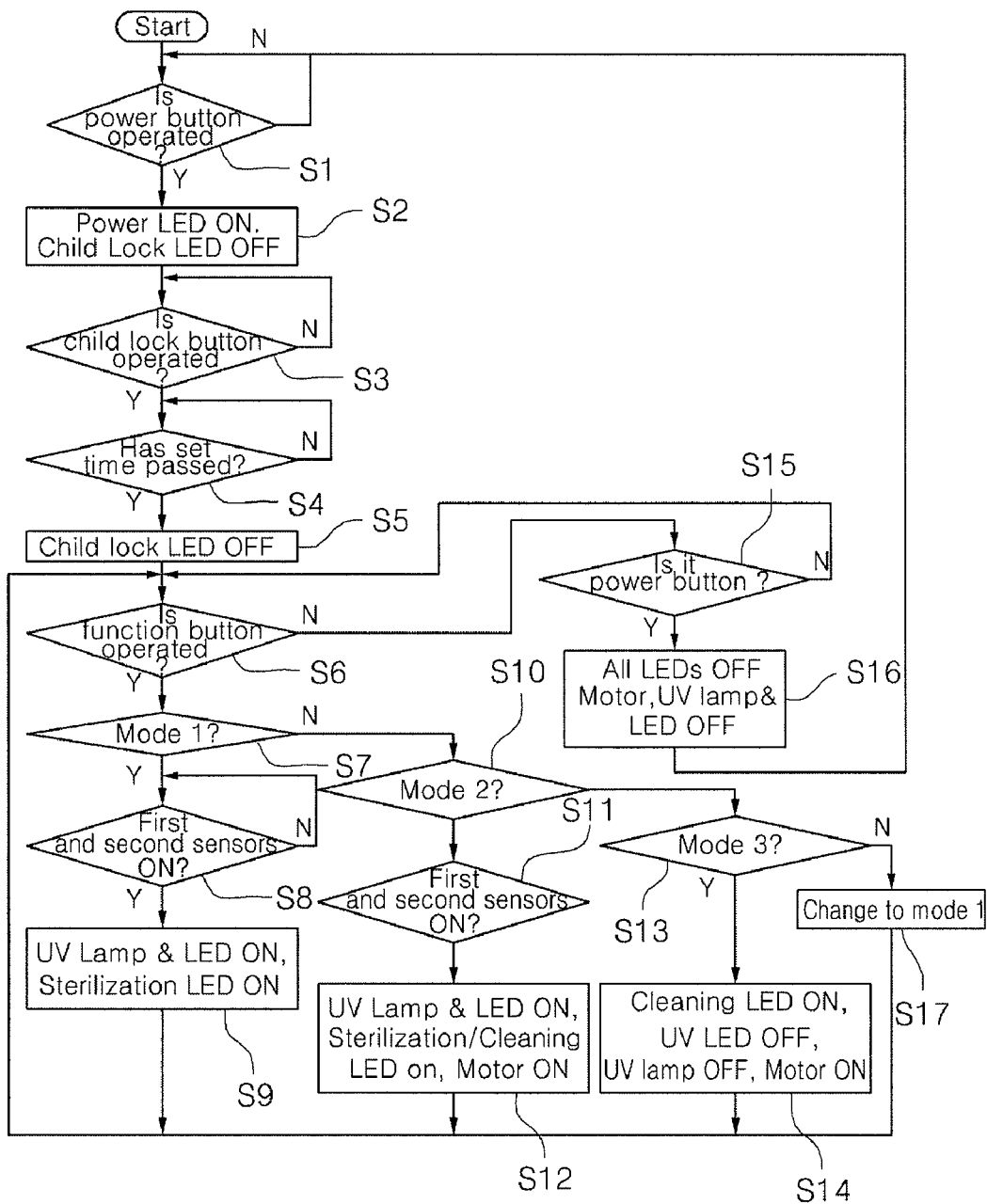

[Figure 11]
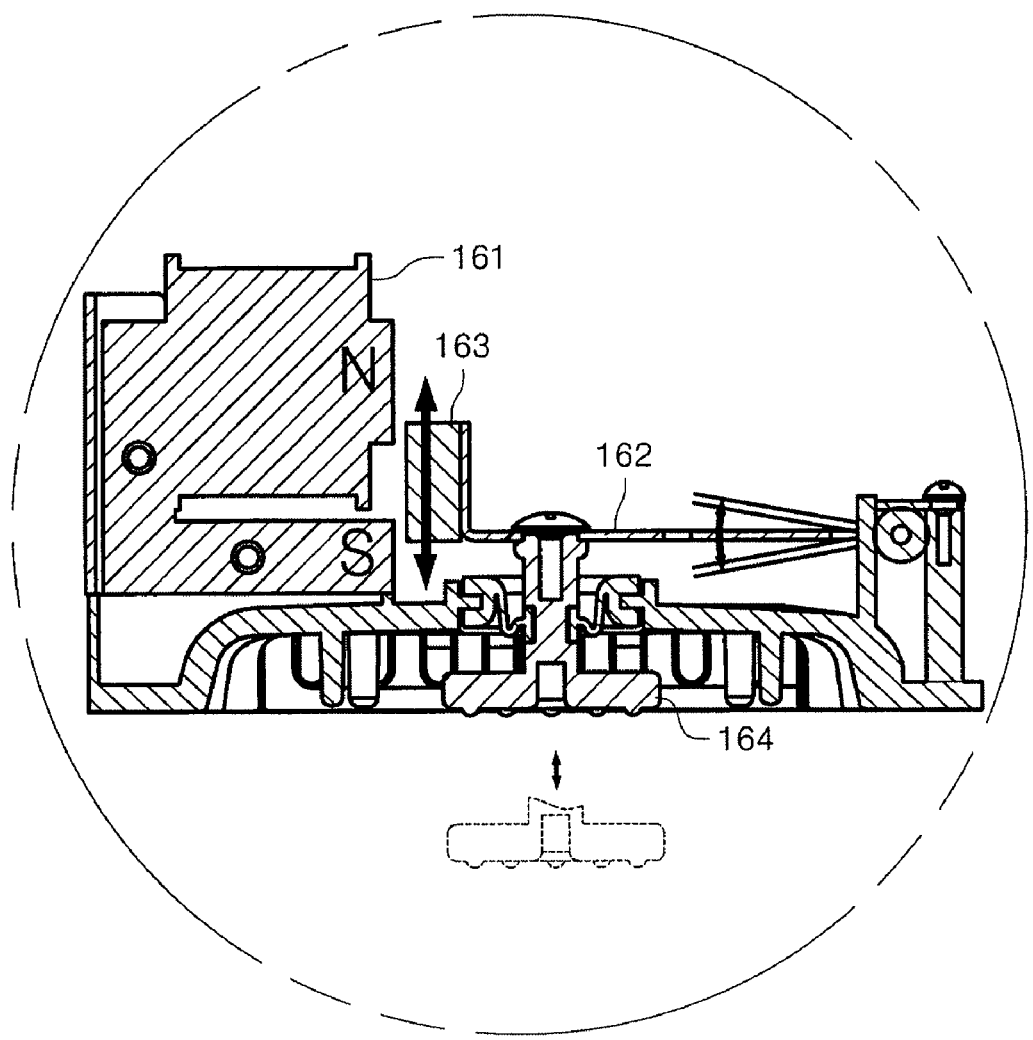

[Figure 12]
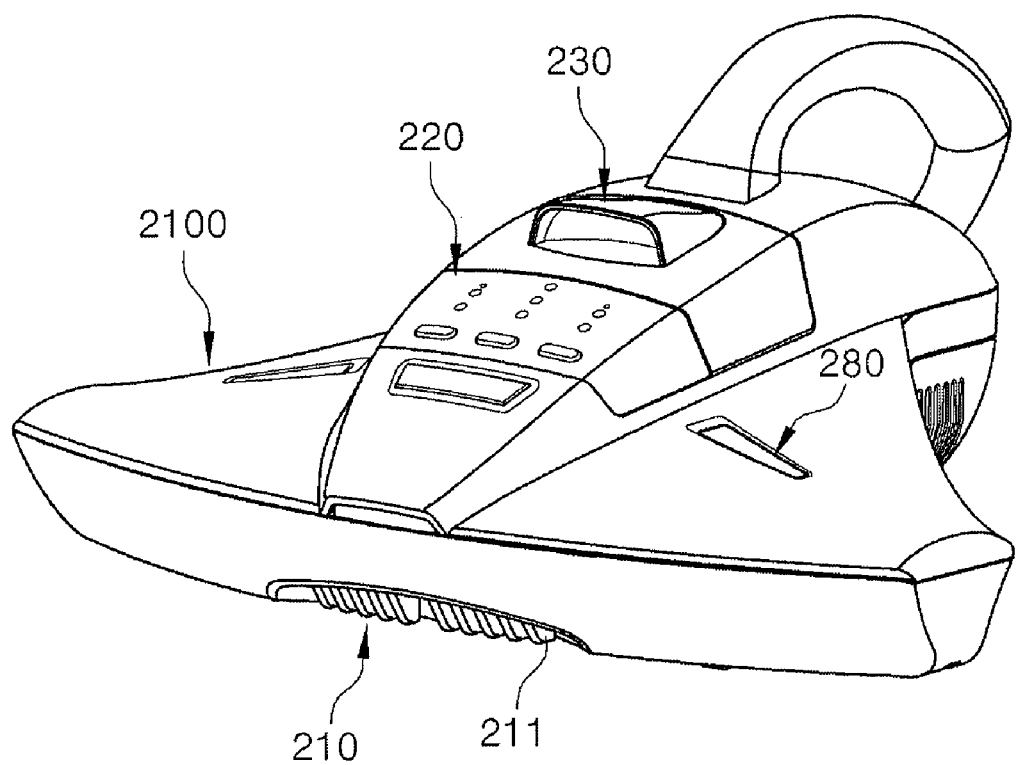

[Figure 13]
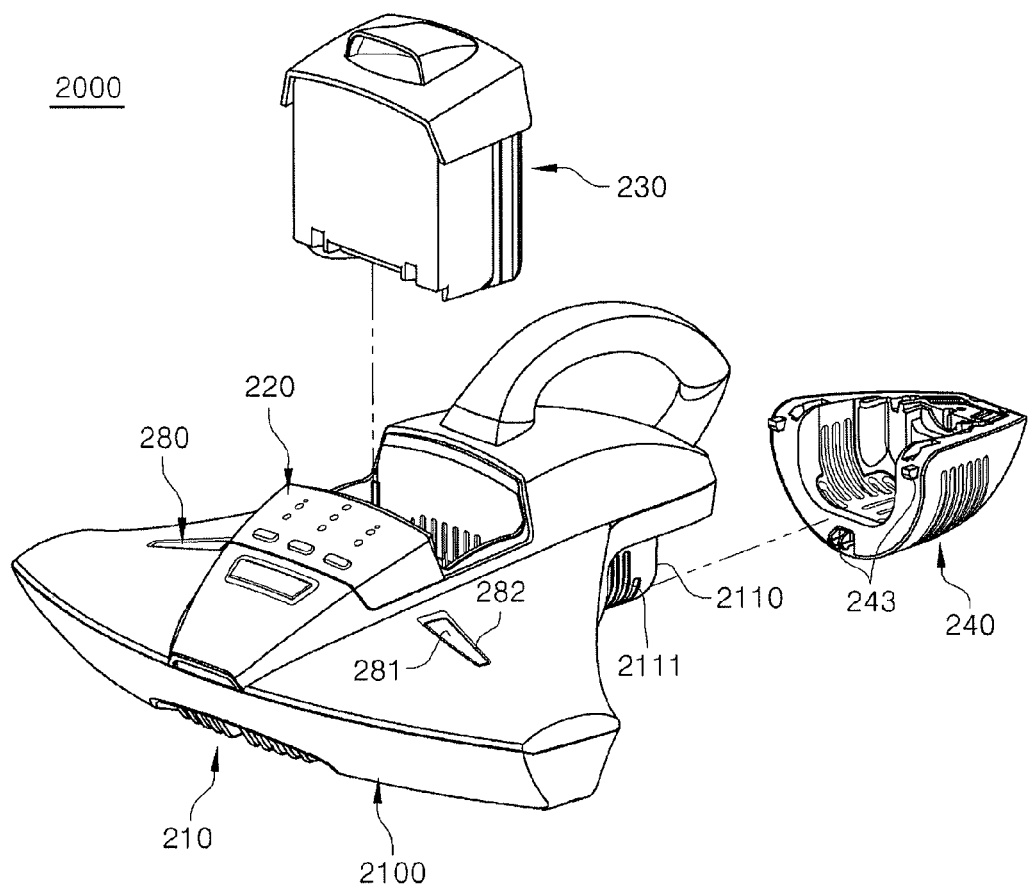

[Figure 14]
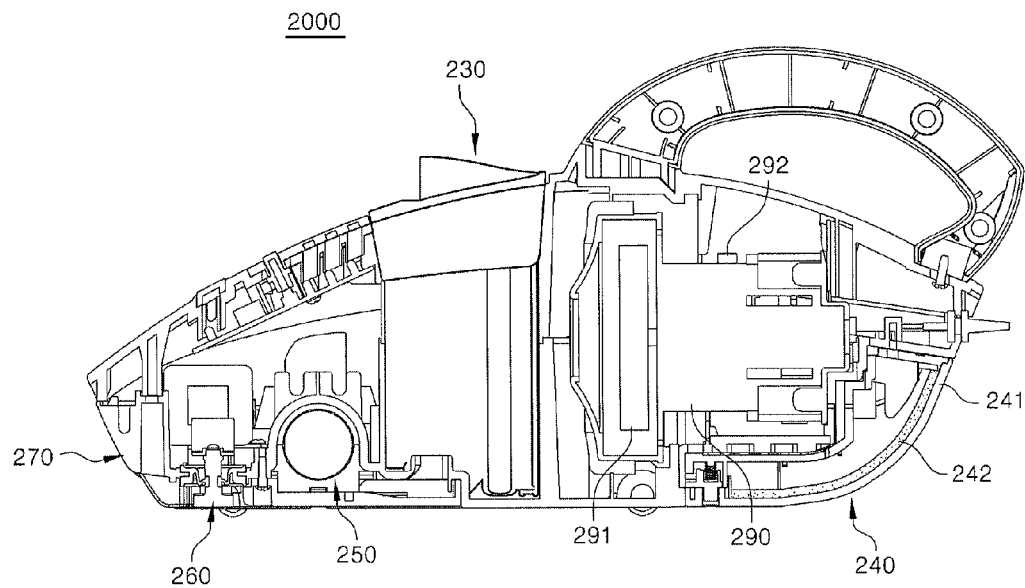

[Figure 15]
(a)
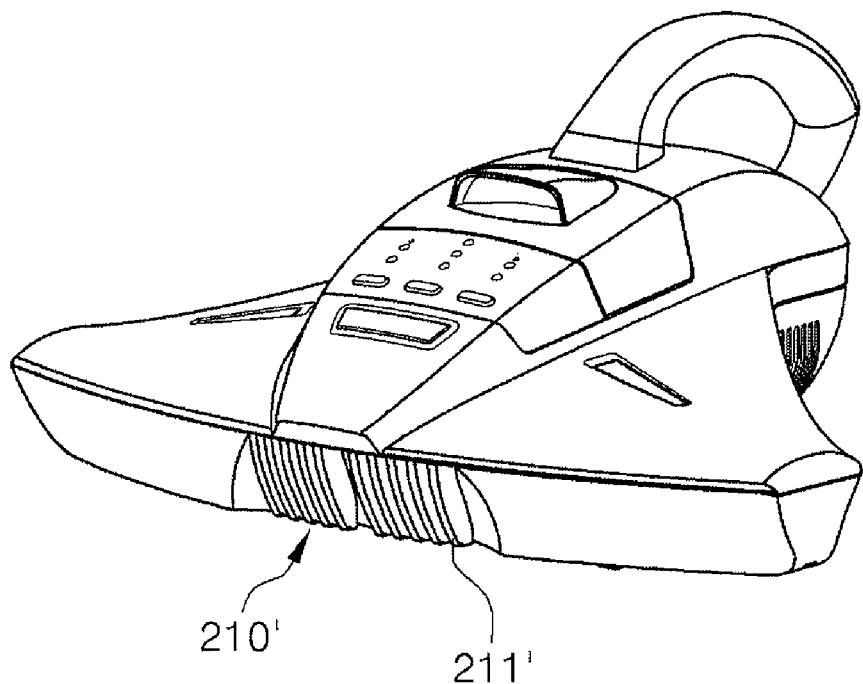
(b)
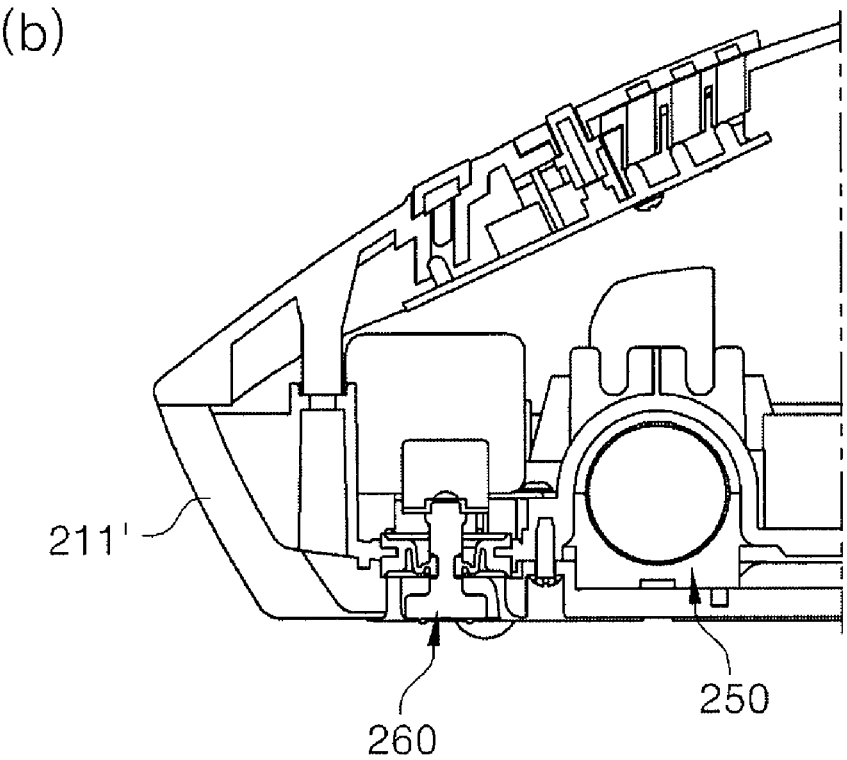

[Figure 16]
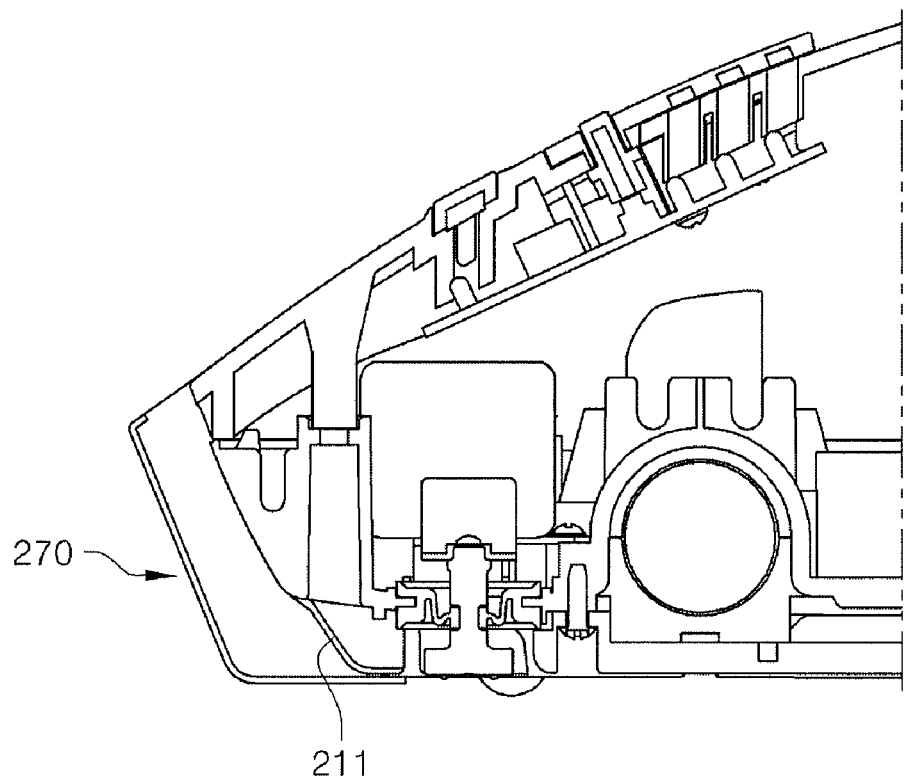
270
211
[Figure 17]
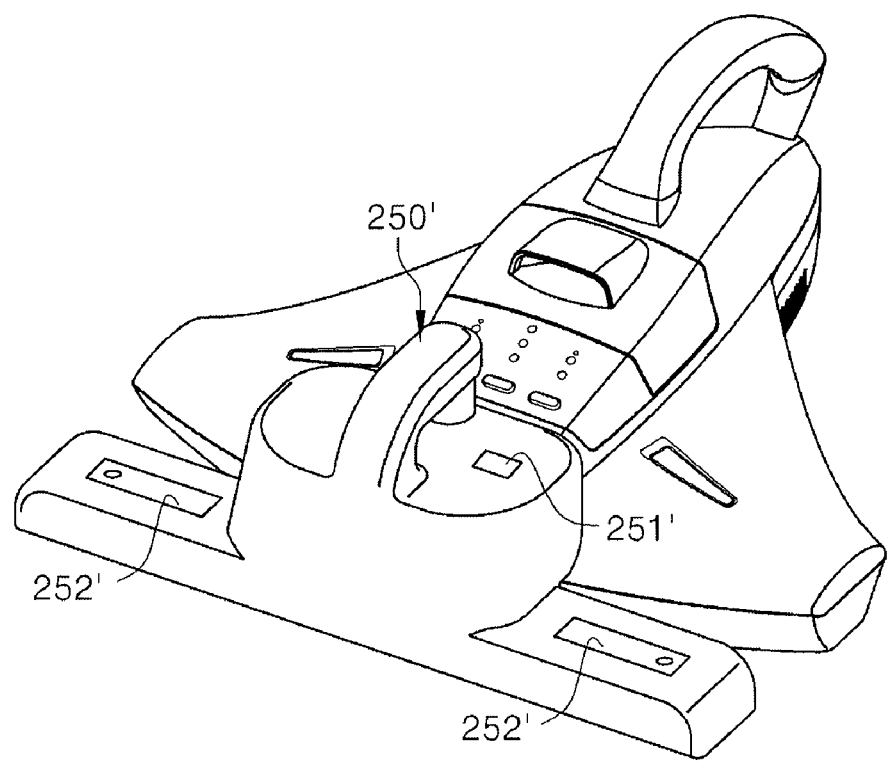
250'
251'
252'
252'

[Figure 18]
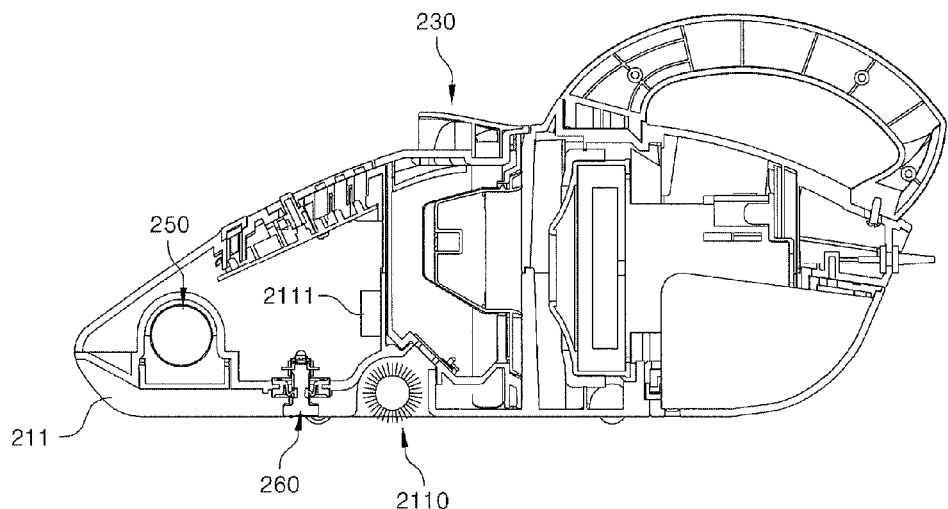
[Figure 19]
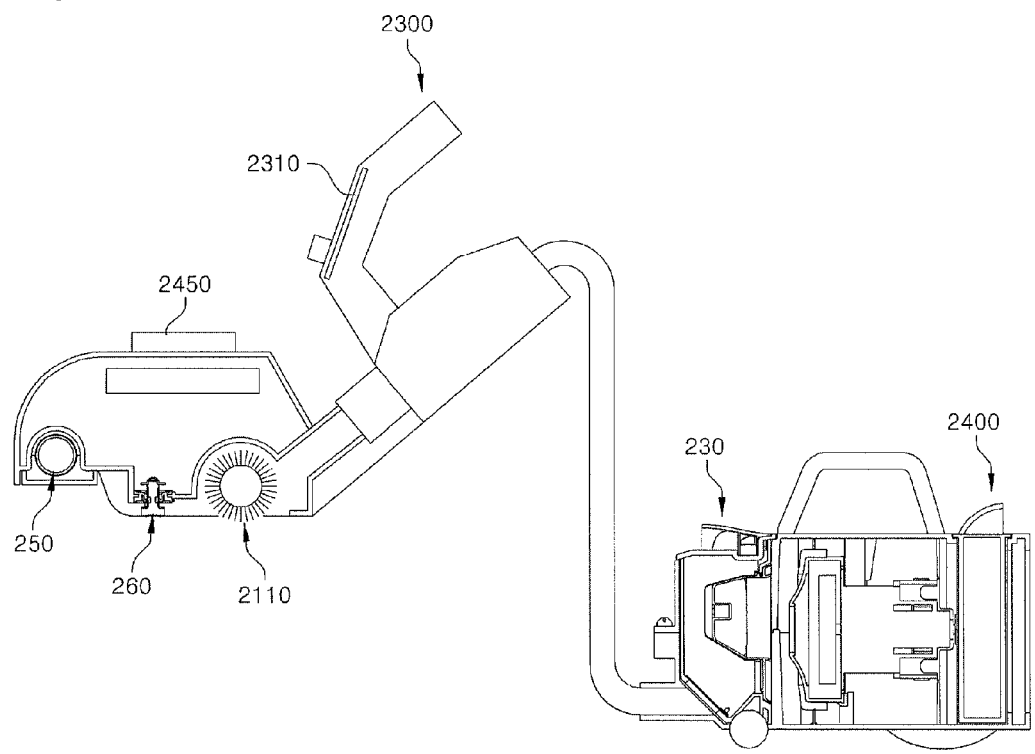

[Figure 20]
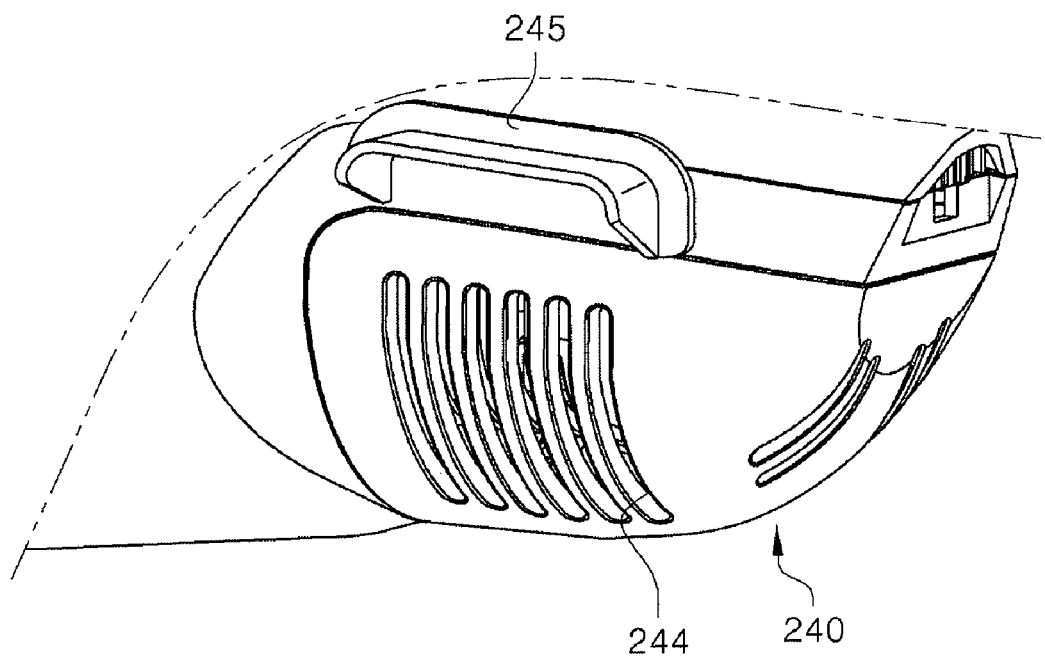

[Figure 21]
(a)
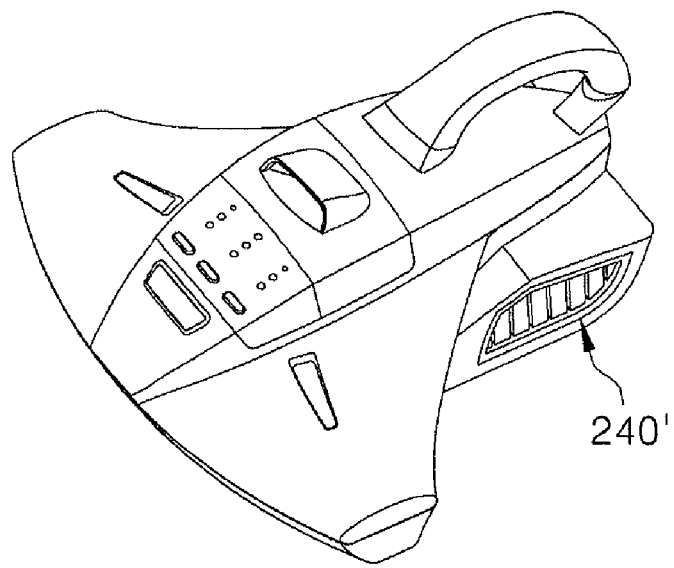
(b)
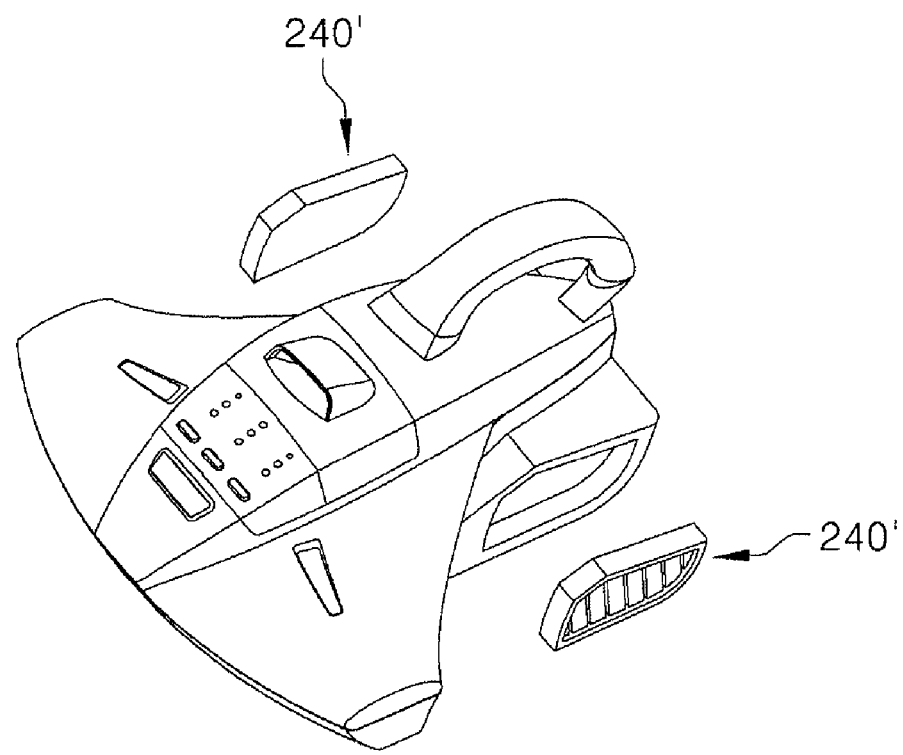

[Figure 22]
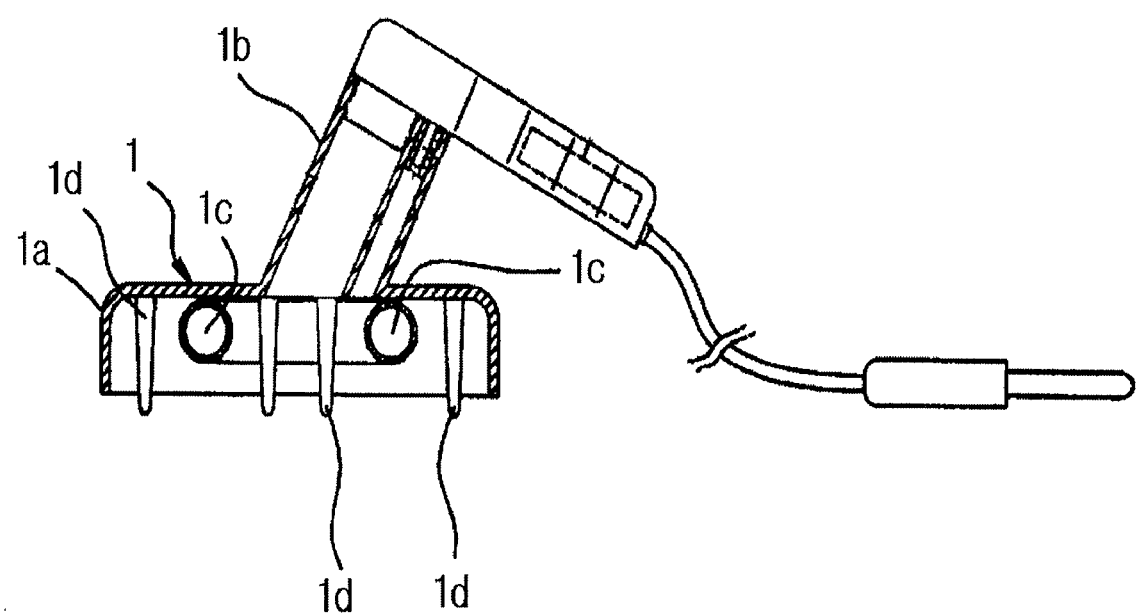

VACUUM CLEANER

CROSS-REFERENCE TO RELATED PATENT APPLICATIONS

This application is a continuation application under 35 U.S.C. §365(c) of International Application No. PCT/KR2006/001745, filed May 10, 2006 designating the United States. International Application No. PCT/KR2006/001745 was published in English as WO2006/121286 A1 on Nov. 16, 2006. This application further claims the benefit of the earlier filing dates under 35 U.S.C. §365(b) of Korean Patent Application Nos. 10-2005-0039553 filed May 12, 2005 and 10-2005-0087990 filed Sep. 22, 2005. This application incorporates herein by reference the International Application No. PCT/KR2006/001745 including the International Publication No. WO2006/121286 A1 and the Korean Patent Application Nos. 10-2005-0039553 and 10-2005-0087990 in their entirety.

BACKGROUND

1. Field

The present disclosure relates to a vacuum cleaner, more particularly, to a vacuum cleaner for bed cloths.

2. Discussion of the Related Technology

Generally, a UV (Ultraviolet) sterilizer uses wavelengths of ultraviolet rays irradiated from a UV lamp to kill DNA and skins of bacteria. FIG. 22 shows a cleaner mounted with an UV lamp. FIG. 22 is a schematic view showing a cleaner equipped with a UV lamp, as disclosed in Korean Laid-Open Patent Publication No. 10-2004-0100409.

A plurality of UV lamps 1c are installed in a main body 1a of an suction plate 1 with the open bottom, and a plurality of protrusions 1d are formed to protrude downward from an upper surface within the main body 1a such that they can be brought into contact with to lower ends of carpet piles in a fabric member such as a carpet.

The foregoing discussion is to provide general background information, and does not constitute an admission of prior art.

SUMMARY

One aspect of the invention provides a vacuum cleaner, which comprises: a housing comprising a bottom, a top and a side interconnecting the top and the bottom; at least one bottom opening formed in the bottom of the housing; a cavity formed in the housing in fluid communication with the at least one bottom opening; a suction passage formed in the housing and in fluid communication with the cavity so as to create a negative pressure in the cavity during operation of the vacuum cleaner, wherein the at least one bottom opening is configured to suck outside dust into the cavity when a negative pressure is created in the cavity; at least one auxiliary opening formed on at least one of the side and the top, wherein the at least one auxiliary opening is in fluid communication with the cavity; wherein the at least one auxiliary opening is configured to permit a substantial air flow therethrough to the cavity throughout operation of the vacuum cleaner.

In the foregoing vacuum cleaner, the housing may comprise a plurality of ribs arranged so as to provide the at least one auxiliary opening. The plurality of ribs may further provide at least one air flow channel to connect to the cavity. The top and the side of the housing may not have a discrete boundary therebetween. The suction passage may comprise an inlet open to the cavity. The substantial air flow from the at least one auxiliary opening to the cavity may be to prevent the negative pressure created in the cavity from being excessive. The vacuum cleaner may further comprise an ultra violet light source configured to irradiate ultra violet light to a surface under the bottom. The vacuum cleaner may further comprise an ultra violet light source configured to irradiate ultra violet light to air being transferred through the suction passage.

Still in the foregoing vacuum cleaner, the vacuum cleaner may further comprise a hitting duster configured to beat a surface under the bottom. The hitting duster may comprise a head configured to make repeated movements to the surface and back to the housing through a hitting duster opening formed in the bottom of the housing. The hitting duster may further comprise an actuator connected to the head and configured to actuate the movements of the head. The vacuum cleaner may further comprise: a first filter located at a first position within the suction passage and configured to filter air flowing through the suction passage; and a second filter located at a second position within the suction passage downstream the first position and configured to further filter the air flowing through the suction passage past the first filter. The vacuum cleaner may further comprise a heater configured to heat air being transferred through the suction passage.

Another aspect of the invention provides a method of vacuum cleaning, which comprise: placing the vacuum cleaner of Claim 1 over a surface such that the bottom faces the surface to clean; and operating the vacuum cleaner so as to create a negative pressure in the cavity, thereby sucking dust and particles into the cavity from the surface via the at least one bottom opening, and thereby creating a substantial air flow into the cavity via the at least one auxiliary opening.

In the foregoing method, the surface may comprise a mattress surface or a bedding surface made of a fabric. The vacuum cleaner may further comprise an ultra violet source, wherein the method may further comprise irradiating ultra violet light onto the surface during the operation. The vacuum cleaner may further comprise a hitting duster, wherein the method may further comprise hitting the surface during the operation. The substantial air flow from the at least one auxiliary opening to the cavity may be to prevent the negative pressure created in the cavity from being excessive. The housing may comprise a plurality of ribs arranged so as to provide the at least one auxiliary opening. The suction passage may comprise an inlet open to the cavity.

One aspect of the invention provides a vacuum cleaner, which comprises: a housing comprising a bottom and a side; a passage formed in the housing and in fluid communication with a dust container; at least one bottom opening formed on the bottom and in fluid communication with the passage; and at least one side opening formed on the side, wherein the at least one side opening is configured to permit a substantial air flow therethrough to the passage even if all openings formed on the bottom comprising the at least one bottom opening are blocked.

In the foregoing vacuum cleaner, the housing may comprise a plurality of ribs defining the at least one side opening on the side. The plurality of ribs may further define at least one air flow channel in fluid communication with the at least one bottom opening. The at least one side opening may be in fluid communication with the passage. The passage may comprise an inlet open to a cavity, wherein the at least one bottom opening is in fluid communication with the passage via the cavity. The passage may comprise an inlet open to a cavity, wherein the at least one side opening is in fluid communication with the passage via the cavity. The vacuum cleaner may further comprise an ultra violet light source configured to irradiate ultra violet light through the at least one bottom opening. The vacuum cleaner may further comprise an ultra violet light source configured to irradiate ultra violet light toward air in the passage.

Still in the foregoing vacuum cleaner, the vacuum may further comprise a hitting duster configured to beat a surface under the bottom. The hitting duster may comprise a head configured to make a repeated movement away from and back to the housing via the at least one bottom opening. The hitting duster may comprise a head and an actuator connected to the head and configured to actuate the movement of the head. The vacuum cleaner may further comprises: a first filter located at a first position and configured to filter air flowing through the passage; and a second filter located at a second position which is downstream from the first position and configured to further filter the air flowing through the passage past the first filter. The vacuum cleaner may further comprise a heat sterilizer configured to apply heat to air in the passage between the first and second filters.

Another aspect of the invention provides a vacuum cleaner, which comprise: a housing comprising a bottom; a passage formed in the housing and in fluid communication with a dust container; at least one bottom opening formed in the bottom and in fluid communication with the passage; and at least one top opening in fluid communication with the passage, wherein the at least one top opening is configured to permit a substantial air flow therethrough to the passage even if all openings formed in the bottom comprising the at least one bottom opening are blocked.

In the foregoing vacuum cleaner, the at least one top opening may be in fluid communication with the passage. The passage may comprise an inlet open to a cavity, wherein the at least one bottom opening may be in fluid communication with the passage via the cavity. The passage may comprise an inlet open to a cavity, wherein the at least one top opening is in fluid communication with the passage via the cavity. The vacuum cleaner may further comprise an ultra violet light source configured to irradiate ultra violet light through the at least one bottom opening. The vacuum cleaner may further comprise an ultra violet light source configured to irradiate ultra violet light toward air in the passage. The vacuum cleaner may further comprise a hitting duster configured to beat a surface under the bottom.

One aspect of the present invention provides a sterilizer for bed clothes in which no vacuum is created even though a fabric member adheres thereto due to a suction force applied to a cleaning object, such as bedding, bed sheet and carpet, which can be easily deformed at its contact surface and contain a great deal of fabric contaminants, whereby the sterilizer can be easily move on the cleaning object.

Another aspect of the present invention provides a sterilizer for bed clothes capable of hitting a cleaning object such as bed clothes such that bacteria, harmful insects or dust inhabiting or adhering between yarns of a fabric member can be removed and eliminated from the cleaning object.

A further aspect of the present invention provides a sterilizer for bed clothes which includes an inner filter and a means provided in a discharge port for eliminating harmful insects and bacteria such that insect sterilization or disinfection efficiency can be enhanced.

A still further aspect of the present invention provides a sterilizer for bed clothes which includes an inner filter and a filter provided in the discharge port for eliminating harmful insects and bacteria such that insert sterilization or disinfection efficiency can be enhanced.

A still further aspect of the present invention provides a sterilizer for bed clothes to which a UV irradiating means can be detachably installed such that only ultraviolet rays can be irradiated to provide a user with convenience of use.

One aspect of the present invention provides a sterilizer for bed clothes, comprising a housing including an ultraviolet (UV) irradiating space depressed into a bottom surface thereof, a suction port formed in the UV irradiating space, a discharge port formed in a side surface thereof, an air passage for connecting the suction port and the discharge port, and a sticking prevention passage depressed into the bottom within the UV irradiating space and extending to the side surface to prevent an object to be sterilized from adhering to the bottom surface; a first UV light emitting means installed in the housing to irradiate ultraviolet rays to the UV irradiating space of the housing; a fan installed in the air passage to discharge air from the suction port to the discharge port; a motor for driving the fan; a filter unit installed on the air passage to purify foreign substances in the air flowing from the suction port to the discharge port; an operating unit for outputting a command signal to control the motor and the first UV light emitting means; and a control unit for receiving the command signal from the operating unit and controlling the motor and the first UV light emitting means.

In the sterilizer for bed clothes, the sticking prevention passage extends to a portion of the bottom surface and the side surface adjacent to the bottom surface. Thus, even though the sticking prevention passage positioned at the bottom surface is closed up by a fabric material, air can be sucked up through the sticking prevention passage positioned at the side surface of the housing.

The sterilizer may further comprise at least one proximity sensor installed to the bottom surface of the housing to detect the presence of the sterilizing object, and the control unit may receive an output signal from the proximity sensor and control the first UV light emitting means and the motor.

The sterilizer includes a plurality of IR sensors installed to the bottom surface of the housing. In such a case, the sterilizer determines that there is no object approaching in front of a light emitting end, i.e. a cleaning object, if a light receiving end does not detect infrared rays emitted from the light emitting end, whereas the sterilizer determines that an object exists if the light receiving end detects the infrared rays. That is, since the sterilizer stops its operation if there is no object, the convenience can be provided to the users.

The sterilizer may further comprise a hitting unit protruding from the interior of the housing toward the bottom surface to hit the sterilizing object. Preferably, the hitting unit includes a magnet installed in the housing, an electromagnet installed adjacent to the magnet, a swinging bar whose one end is hinged and the other end is coupled with the electromagnet such that the swinging bar can be shaken vertically as a polarity of the electromagnet alternates, and a hitting rod installed to the swinging bar to hit the sterilizing object as the swinging bar is vertically shaken. Further, the hitting rod may be installed on the sticking prevention passage of the housing to protrude therefrom, and the control unit may receive the command signal from the operating unit to apply electric power to the electromagnet and to control changing the polarity.

When a bed cloth such as bedding or carpet is sterilized or cleaned, the small harmful insects and dust adhering to the surface of the bedding or carpet can be detached from the surface by means of the hitting unit, and the detached small harmful insects and dust can be sterilized (killed) or sucked up (removed), so that the sterilizing and cleaning efficiency can be enhanced.

Further, a plurality of rounded protrusions protruding vertically from the interior of the housing to the outside may be included in the sticking prevention passage, and the plurality of protrusions may be spaced apart inward from the bottom surface of the housing by a predetermined regular interval or protrude further outward from the bottom surface of the housing by a predetermined interval.

Since the protrusions are further formed in the sticking prevention passage, they can be brought into contact with even lower ends of piles of the bed clothes such as carpet to allow the small harmful insects and dust to be removed from the bed clothes.

The sterilizer may further comprise a second UV light emitting means installed adjacent to the filter unit in the housing to kill small harmful insects filtered out by the filter unit, and a heater installed adjacent to the discharge port in the housing to heat and remove the small harmful insects in the air discharged through the discharge port, wherein the control unit receives the command signal from the operating unit and controls the second UV light emitting means and the heater.

The sterilizer further includes a UV LED installed adjacent to the filter unit in addition to the UV lamp. The sterilizer also includes a heater adjacent to the discharge port. Therefore, the small harmful insects introduced into the housing of the sterilizer can be exterminated twice or three times.

The sterilizer may further comprise a display unit which is installed to an outer surface of the housing and includes a plurality of light emitting diodes (LEDs) to indicate whether UV lamps, UV LEDs and the motor are operated, wherein the control unit receives the command signal from the operating unit and controls turning on or off the plurality of LEDs.

In the sterilizer, the sticking prevention passage may be provided with a plurality of ribs formed to surround the sticking prevention passage from a starting point to an ending point of the sticking prevention passage.

Since the plurality of ribs are formed or installed to surround the sticking prevention passage such that air passage toward the sticking prevention passage can be ensured, the air passage is still maintained by means of the ribs even though a fabric member sticks to the passage due to a suction force.

Another aspect of the present invention provides a sterilizer for bed clothes, comprising a UV irradiating unit provided with a UV lamp for emitting ultraviolet rays; a housing including a suction port formed to suck up outside air, a discharge port formed in a side surface of the housing, an air passage for connecting the suction port and the discharge port, and a sticking prevention passage extending to a portion of the bottom surface and the side surface of the housing to prevent a sterilizing object from sticking to the bottom surface of the housing; a motor including a fan installed in the housing to discharge air from the suction port to the discharge port through the air passage; a first filter unit installed on the air passage between the suction port and the motor; and a second filter unit installed on the air passage between the motor and the discharge port to filter out foreign substances in the air passed through the first filter unit and the motor and then to sterilize and kill bacteria and harmful insects in the filtered foreign substance using a portion of heat generated in the motor but not emitted to the outside. Preferably, a motor seating unit which partially protrudes outward to allow the motor to be placed thereon and is formed with a plurality of discharge holes for discharging air introduced by the motor is further formed in the housing, and the second filter unit is detachably installed to an outer surface of the housing to surround the motor seating unit. More preferably, the second filter unit includes a case and a filter installed within the case, and the filter has lower air permeability than that of the first filter unit. That is, the second filter unit has a function of purifying the foreign substances in the air passed through the fan of the motor and of sterilizing or killing the small harmful insects or bacteria filtered out by the filter unit using heat generated in the motor. At this time, the motor is further provided with an overheating prevention means. Thus, even though the heat from the motor is not released and overheated by the second filter unit, the overheating prevention means can prevent the occurrence of the overheating and the resultant accident.

The sterilizer may further comprise a hitting unit which protrudes from the interior of the housing toward the bottom surface to hit the sterilizing object. Dust or small harmful insects strongly adhering to surfaces of bed clothes may be detached from the surfaces by means of the hitting unit and then sucked up by means of the suction force of the fan caused by the rotation of the motor. Thus, the dust or small harmful insects existing on the surface of the bed cloth can be easily removed. The hitting means may be configured in such a manner that an electromagnet and a permanent magnet are provided and a swinging bar mounted with a hitting rod is shaken to hit the cleaning object as the polarity of the electromagnet alternates. Alternatively, a vibration motor may be used to shake the swinging bar.

In the sterilizer, the UV irradiating unit may be installed in the housing or detachably installed to an upper surface of the housing to allow ultraviolet rays to be emitted toward the bottom surface of the housing. The UV irradiating unit detachably installed to the upper surface of the housing may be detached and used when only the UV sterilization is executed. Thus, the UV irradiating unit preferably includes an additional battery for supplying electric power and a switch for turning on/off the UV lamp.

Furthermore, although the sticking prevention passage is formed to extend to the bottom surface and the side surface adjacent to the bottom surface of the housing, the bed clothes may be pushed to close up even the sticking prevention passage. Thus, a plurality of ribs or an additional cap is preferably installed to extend from the sticking prevention passage to the upper surface of the housing. At this time, in a case where the plurality of ribs are formed or installed, air can be introduced between the ribs or between the upper surface of the housing and the ribs. In a case where the additional cap is installed, it is preferably brought into contact and communication with the sticking prevention passage and installed to surround the housing with a predetermined interval, so that an air introduction passage can be ensured.

In a case where the UV irradiating unit is installed within the housing, a display window is further installed on the upper surface of the housing such that it can be confirmed from the outside whether the UV lamp installed in the housing is operated. Preferably, the display window includes a hole and a member for transmitting visible light but blocking the ultraviolet rays from the UV lamp such that it can be easily confirmed from the outside whether the UV lamp is operated.

A further aspect of the present invention provides a sterilizer for bed clothes, comprising a UV irradiating unit provided with a UV lamp for emitting ultraviolet rays; a housing including a suction port formed to suck up outside air, a discharge port formed in a side surface of the housing, an air passage for connecting the suction port and the discharge port, and a sticking prevention passage extending to a portion of the bottom surface and the side surface of the housing to prevent a sterilizing object from sticking to the bottom surface of the housing; a motor including a fan installed in the housing to discharge air from the suction port to the discharge port through the air passage; a hitting unit mounted in the housing to protrude toward the bottom so as to hit the sterilizing object; and a hitting unit protruding from the interior of the housing toward the bottom surface to hit the sterilizing object, wherein the hitting unit is installed at a front end of the suction port in an air introduction direction, and the UV irradiating unit is installed to a front end of the hitting unit in the housing and spaced apart from the bottom surface by a predetermined interval.

The sterilizer may further comprise a brush unit installed between the hitting unit and the suction port to sweep foreign substances on a surface of the cleaning object. Preferably, the brush unit includes a brush installed to protrude slightly from the bottom surface of the housing, and a motor installed in the housing at a position adjacent to the brush for rotating the brush.

BRIEF DESCRIPTION OF THE DRAWINGS

FIG. 1 is a perspective view showing a sterilizer according to an embodiment of the present invention.

FIG. 2 is a perspective bottom view showing the sterilizer according to an embodiment of the present invention.

FIG. 3 is a sectional view taken along line A-A of FIG. 1.

FIG. 4 is an exploded perspective view illustrating a filter unit of the sterilizer according to an embodiment of the present invention.

FIG. 5 is a view showing a suction prevention passage of a sterilizer according to an embodiment of the present invention.

FIG. 6 is a view showing a moving means of the sterilizer according to an embodiment of the present invention.

FIG. 7 is a block diagram illustrating a control operation of the sterilizer according to an embodiment of the present invention.

FIG. 8 is a view showing an operating unit of the sterilizer according to an embodiment of the present invention.

FIG. 9 is a circuit diagram illustrating an infrared (IR) sensor unit of the sterilizer according to an embodiment of the present invention.

FIG. 10 is a flowchart illustrating an operation of a control unit of the sterilizer according to an embodiment of the present invention.

FIG. 11 is an enlarged sectional view illustrating an A portion of FIG. 2.

FIG. 12 is a perspective view showing a sterilizer for bed clothes according to an embodiment of the present invention.

FIG. 13 is a partially exploded perspective view showing the sterilizer for bed clothes according to an embodiment of the present invention.

FIG. 14 is a sectional view showing the sterilizer for bed clothes according to an embodiment of the present invention.

FIG. 15 is a perspective view and a partial sectional view showing a sterilizer for bed clothes according to an embodiment of the present invention.

FIG. 16 is a partial sectional view showing a sterilizer for bed clothes according to an embodiment of the present invention.

FIG. 17 is a perspective view showing a sterilizer according to an embodiment of the present invention.

FIG. 18 is a sectional view illustrating a sterilizer for bed clothes according to an embodiment of the present invention.

FIG. 19 is a view illustrating a sterilizer for bed clothes according to an embodiment of the present invention.

FIG. 20 is a view illustrating a sterilizer for bed clothes according to an embodiment of the present invention.

FIG. 21 is a view illustrating a sterilizer for bed clothes according to an embodiment of the present invention.

FIG. 22 is a schematic view illustrating a cleaner including an exemplary UV lamp.

DETAILED DESCRIPTION OF EMBODIMENTS

Hereinafter, various embodiments of the present invention will be described in detail with reference to the accompanying drawings. FIG. 1 is a perspective view showing a sterilizer according to an embodiment of the present invention, FIG. 2 is a perspective bottom view showing the sterilizer according to an embodiment of the present invention, FIG. 3 is a sectional view taken along line A-A of FIG. 1, and FIG. 4 is an exploded perspective view illustrating a filter unit of the sterilizer according to an embodiment of the present invention.

A sterilizer 1000 of the present embodiment comprises a housing 100 including an ultraviolet (UV) irradiating space 52 depressed into a bottom surface thereof, a suction port (not shown) formed in the UV irradiating space 52, a discharge port 90 formed in a side surface thereof, an air passage (not shown) for connecting the suction port and the discharge port 90, and a sticking prevention passage 10 depressed into the housing within the UV irradiating space 52 and extending to the side surface of the housing to prevent an object to be sterilized from adhering to the bottom surface; an operating unit 20 installed to an upper surface of the housing 100 to convert an external input into an electric signal; and a handle 40 installed to an upper portion of the housing 100. Within the housing 100, a motor 80 mounted with a fan 81 is installed along the air passage to generate a suction force. A UV lamp 50 which is mounted within the housing 100 for emitting ultraviolet rays to the outside and a detachable filter unit 30 which can be detached in a direction toward the upper surface of the housing 100 and filter out foreign substances in the air sucked in through the sticking prevention passage 10 upon the operation of the motor 80 are installed at a front end of the fan 81 within the air passage. In addition, the sterilizer further comprises a UV LED 130 installed adjacent to the filter unit 30 of the housing 100 to sterilize small harmful insects filtered out by the filter unit 30 and a heater 110 installed adjacent to the discharge port 90 of the housing 100 to heat and kill small harmful insects in the air discharged through the discharge port 90. Wheels 60 are further installed to the bottom surface of the housing 100 to allow the sterilizer to be easily traveled.

An A portion of FIG. 2 is shown in FIG. 11 in detail. The sterilizer 1000 of this embodiment further comprises a hitting unit 160 installed to protrude from the bottom surface of the housing 100 to hit a cleaning object. The hitting unit 160 includes a magnet 161 installed within the housing 100, an electromagnet 163 installed adjacent to the magnet 161, a swinging bar 162 whose one end is hinged and the other end is coupled with the electromagnet 163 such that it can be shaken vertically by the magnet 161 as the polarity of the electromagnet 163 is alternated, and a hitting rod 164 installed to the swinging bar 162 to protrude into the sticking prevention passage 10 of the housing 100 such that it can hit the cleaning object as the shaking bar 162 is vertically shaken.

The sticking prevention passage 10 includes a plurality of rounded protrusions 11 protruding downward in the housing 100 in a vertical direction, and the protrusions 11 protrude inward from the bottom surface of the housing 100 at regular intervals. However, the present invention is not limited thereto. That is, the protrusions may protrude further outward from the bottom surface of the housing at regular intervals.

The interior of the housing 100 is partitioned into a region where the sticking prevention passage 10 is formed and another region where the filter unit 30 and the UV LED 130 are installed. A check valve 140 that is opened only in one direction is installed to the filter seating unit 150 such that air sucked in through the sticking prevention passage 10 by the operation of the motor 80 doe not flow back toward the sticking prevention passage 10. A sensor unit 70 including a plurality of IR sensors is provided onto the bottom surface of the housing 100 to detect the presence of a cleaning object approaching the sterilizer. In addition, in order to indicate whether the UV lamp 50, the UV LED 130 and the motor 80 are operated, a display unit including a plurality of LEDs 24 to 28 is further installed to an external surface of the housing 100. In this embodiment, an example in which the display is integrally formed with the operating unit 20 will be described.

Reference numerals 120 and 140 designate a motor seating unit and a heater seating unit, respectively.

In addition, the sterilizer 1000 of this embodiment comprises a control unit 200 which receives a signal output from the operating unit and then sends predetermined control signals to the UV lamp 50, the heater 110 and the motor 80, respectively. Further, the control unit 200 sends stop control signals to the UV lamp 50, the UV lamp 50 and the motor 80 if a detection signal is not input from the sensor unit 70. The control unit also receives an output signal of the operating unit 20 to send a signal for controlling turning on or off the plurality of LEDs 24 to 28 and to apply electric power to the electromagnet 163. Furthermore, the control unit outputs a control signal to allow the polarity of the electromagnet to be alternated.

FIGS. 1-5 illustrate the sticking prevention passage 10 that includes openings 500, which define auxiliary openings of the vacuum cleaner 1000. The openings 500 are configured to permit a substantial airflow therethrough during operation of the vacuum cleaner. FIGS. 2 and 5 illustrate bottom views of the vacuum cleaner 1000, in which one or more cavities 600a and 600b formed in the bottom of the vacuum cleaner 1000. FIGS. 2 and 5 also show suction passageways 700a and 700b that are formed in the vacuum cleaner 1000 that is in fluid communication with the cavities 600a and 600b, respectively.

The filter unit 30 can be detachably installed to an upper portion of the housing 100. As shown in FIG. 4, the filter unit 30 includes a filter body 31, a filter 33 and a lid 32. When a user intends to exchange the filter 33 or clean the filter unit 30, the lid 32 is removed such that the filter 33 can be easily exchanged or the filter unit 30 can also be cleaned.

In order to eliminate small harmful insects inhabiting bed clothes such as bedding, the sterilizer 1000 of this embodiment turns on the UV lamp 50 to sterilized the small harmful insects and operates the motor 80 to suck up the dust or small harmful insects and then to filter out the dust and insects by means of the filter 33. At this time, since the plurality of protrusions 11 are formed in the sticking prevention passage 10 and the sticking prevention passage 10 extends from the bottom surface to a side surface 12 of the housing, an air passage is still established toward the side surface 12 and thus not closed up even though a fabric material adheres to the bottom surface of the housing due to the suction force of the motor 80.

Although it has been illustrated in this embodiment that the plurality of protrusions 11 are formed in the sticking prevention passage 10, the present invention is not limited thereto. That is, a plurality of ribs may be formed to surround the sticking prevention passage 10 from the side surface to the bottom surface of the housing as shown in FIG. 5.

In addition, the sterilizer 1000 of this embodiment is provided with the hitting unit 160 for hitting a sterilizing and cleaning object to come off small harmful insects and dust from a surface of the object. The hitting unit 160 includes the magnet 161 installed within the housing 100, the electromagnet 163 installed adjacent to the magnet 161, the swinging bar 162 whose one end is hinged and the other end is coupled with the electromagnet 163 such that it can be shaken by means of a magnetic field of the magnet 161 as the polarity of the electromagnet 163 is alternated, and the hitting rod 164 installed at a set position of the swinging rod 162 to allow the object to be hit. The hitting rod 164 protrudes from the sticking prevention passage 10 of the housing 100 and hits the cleaning object to come off the fine dust or small harmful insects adhering to the surface of the cleaning object. Then, the small harmful insects can be sterilized by the UV lamp 50 and the fine dust can be easily removed using the suction force generated by the motor 80.

In addition, the filter seating unit 150 in the housing 100 is partitioned such that it can be isolated from the outside. Further, the filter seating unit is provided with the check valve 140 such that air cannot flow backward and can be introduced only when the air is sucked up by means of the motor 80. In particular, since an additional UV LED 130 is installed to sterilize the small harmful insects filtered out by the filter 33, an effect of sterilizing the small harmful insects can be further enhanced. Moreover, since the heater 110 is installed to the discharge port 90 of the housing 100, the small harmful insects discharged through the discharge port 90 can be heated and eliminated. Therefore, a structure for allowing the small harmful insects to be sterilized three times can be obtained.

FIG. 6 illustrates an embodiment of the present invention in which protrusions 61 or balls 62 are installed to the bottom surface of the housing 100 instead of the wheels 60.

Now, the operations of the control unit and the sensor unit according to an embodiment will be described with reference to FIGS. 7 to 10. The control unit 200 receives signals from the operating unit 20 and the sensor unit 70 and controls the operations of the motor 80, the UV lamp and LED 50 and 130, the heater 110, and the display, i.e. the plurality of LEDs 24 to 28. If a user operates buttons 21, 22 and 23 of the operating unit 20, the control unit 200 outputs a control signal corresponding to the user's operation and thus a lighting signal of the LEDs 24 to 28. It will be explained in more detail with reference to a flowchart of FIG. 10.

If the power button 22 is operated (S1), the control unit 200 receives a power button ON signal and outputs a control signal for turning on the power LED 27 and the child lock display LED 28 (S2). Further, the control unit 200 determines whether the function button 21 and the child lock button 23 are operated at the same time (S3). If the child lock button 23 is turned on over a set time while the function button 21 is in an ON state (S4), the control unit 200 outputs a control signal for releasing a child lock state and turning off the child lock display LED 28 (S5).

Then, the control unit 200 determines whether the function button 21 is operated (S6). In such a state, the control unit 200 also determines whether it is a preset mode according to the number of times the button 21 is pressed. If the function button 21 is not operated, the control unit determines whether the power button 22 is operated (S15). If it is determined that the power button 22 is operated, the control unit 200 turns off the LEDs 24 to 28 of the display, the UV lamp 50, the motor 80, the heater 110 and the electromagnet 163 and then returns to a step S6 in which it is determined whether the function button 21 is operated.

If the function button 21 is operated only once, the control unit 200 determines the current state as a preset sterilizing mode (Mode 1) (S7) and then receives a detection signal from the sensor unit 70 (S8). If ON signals are input from at least two IR sensors among the plurality of IR sensors, the control unit 200 outputs a control signal for turning on the UV lamp 50, the UV LED 130 and the sterilizing LED 24 (S9).

A circuit diagram of the sensor unit 70 is shown in FIG. 9. An arbitrary carrier component is inserted into an output signal at an output side B of the IR sensor to encode the output signal, and the output signal with the carrier component inserted therein is decoded at a light receiving side C using a low pass filter R5 and C1 such that the output signal is not changed due to external noise or disturbance.

If the function button 21 is operated twice, the control unit 200 determines the current state as a preset sterilizing and cleaning mode (Mode 2) (S10) and then receives a detection signal from the sensor unit 70. If ON signals are input from at least two IR sensors among the plurality of IR sensors (S11), the control unit 200 sends an ON operation signal to the UV lamp 50, the UV LED 130, the motor 80 and the electromagnet 163 such that the hitting rod 164 hits a cleaning object to allow the small harmful insects and dust to be detached from the surface of the cleaning object and to be sterilized, and the detached small harmful insects and dust are then sucked up by means of the suction force of the motor 80. As a result, the sterilizing and cleaning processes can be performed at the same time.

If the function button 21 is operated three times, the control unit 200 determines the current state as a preset cleaning mode (Mode 3) and then receives a detection signal from the sensor unit 70. If ON signals are input from at least two IR sensors among the plurality of IR sensors, the control unit 200 sends an ON operation signal to the motor 80 to suck up the dust and the like.

The sensor unit 70 includes the plurality of IR sensors to detect the presence of an object approaching the sterilizer. That is, in a case where the sterilizer 1000 is carried away from a sterilizing and cleaning object by a user, the sterilizer 1000 is not operated even though the function button 21 of the operating unit 20 is operated.

FIGS. 12 to 14 show a sterilizer for bed clothes according to an embodiment of the present invention. That is, FIG. 12 is a perspective view of the sterilizer for bed clothes according to an embodiment of the present invention, FIG. 13 is a partial exploded perspective view of the sterilizer for bed clothes according to an embodiment of the present invention, and FIG. 14 is a sectional view of the sterilizer for bed clothes according to an embodiment of the present invention.

A sterilizer 2000 of this embodiment comprises a housing 2100 which includes a sticking prevention passage 210 extending to a bottom surface and a side surface adjacent to the bottom surface and formed with a plurality of ribs 211 in the extending direction; a operating unit 220 which is installed on an upper surface of the housing 2100 to output an ON/OFF signal for turning on or off the motor 290 and/or the UV irradiating unit 250 in the housing 210 according to an external operation; a hitting unit 260 which is installed in the housing 2100 and protrudes toward the bottom surface of the housing to hit a sterilizing object; a first filter unit 230 which is inserted and installed in an upper portion of the housing 2100 to purify air introduced into the housing 2100 via a suction port (not shown) through the sticking prevention passage 210; and a second filter unit 240 which is detachably installed to surround a motor seating unit 2110 formed in the housing to protrude outward from the interior of the housing and to allow a motor to be seated thereon. A display window 280 is further formed on the upper surface of the housing 2100 such that it can be confirmed from the outside by the naked eyes whether a UV lamp (not shown) of the UV irradiating unit 250 installed in the housing is operated. The display window 280 includes a through-hole 282 and a display member 281 installed in the through-hole 282 to transmit visible light but block ultraviolet rays. A discharge port 2111 is further formed in the motor seating unit 2110 to allow air to be discharged through the discharge port.

The second filter unit 240 includes a case 241 provided with a coupling means 243 for coupling with a coupling hole (not shown) formed in the housing 2100 to surround the motor seating unit 2110, and a filter member 242 installed in the case 241 to filter out foreign substances in the air. The filter member 242 of the second filter unit 240 has air permeability than that of the first filter unit 230.

An overheating prevention unit 292 is further installed to the motor 290. The overheating prevention unit 292 detects heat generated in the motor and then stops the operation of the motor if heat greater than a set temperature is detected for a certain period of time. That is, since the second filter unit 240 is installed to surround the motor seating unit 2110 and the filter member 242 has lower air permeability, the heat generated in the motor can partially exist in the second filter unit 240. Thus, the remaining heat can be used to sterilize the small harmful insects filtered out by the filter member 242. Therefore, if unnecessarily higher heat is generated for a predetermined period of time, the overheating prevention unit 292 stops the operation of the motor to thereby prevent any failure or breakdown caused by the overheating.

The hitting unit 260 can be implemented in various ways. For example, an electromagnet and a permanent magnet are provided in such a manner that a swinging bar mounted with a hitting rod (not shown) is shaken as the polarity of the electromagnet alternates. Alternatively, a hitting rod may be installed such that it can be vertically or horizontally shaken by means of a vibration motor.

In the sterilizer 2000 for bed clothes according to this embodiment of the present invention, the dust and small harmful insects adhering to the surface of bed clothes are detached from the surface by means of a hitting action by the hitting unit 260. Then, air containing the detached dust and small harmful insects is introduced through the suction port by means of a suction force of the fan 291 caused by the operation of the motor and primarily purified in the first filter unit 230. Further, the dust and harmful insects contained in the air passing through the motor are completely eliminated by means of the second filter unit 240. At this time, the small harmful insects are killed by means of the heat generated in the motor.

FIG. 15 is a view showing a sterilizer for bed clothes according to an embodiment of the present invention. Referring to FIG. 15, ribs 211 formed in a sticking prevention passage 210 extend close to an upper surface of the housing 2100. That is, in a case where the bed cloths are thinner, a surface may be pulled up to close up the sticking prevention passage 210 as shown in FIGS. 1 and 2. Thus, the ribs 211 are formed to extend close to the upper surface of the housing such that the sticking prevention passage 210 can be prevented from being closed up by the surface of the bed cloth. Although it has been described in this embodiment that the ribs 211 extend vertically up to the center portion as shown in FIG. 15, the present invention is not limited thereto. That is, the ribs may be formed even on the upper surface of the housing 2100.

FIG. 16 is a view showing a sterilizer for bed clothes according to an embodiment of the present invention. Referring to this figure, an additional sticking prevention cap 270 which are brought into contact with the sticking prevention passage 210 and spaced apart from an outer surface of the housing is installed to surround even the upper surface of the housing, in order to avoid the phenomenon that the air cannot be introduced into the housing because the sticking prevention passage 210 shown in FIGS. 12 and 13 is closed up by a thin bed cloth. Since the sticking prevention cap 270 and the housing 2100 are spaced apart from each other by a predetermined gap, an air flowing passage can be established toward the gap to prevent a vacuum phenomenon from being created. Thus, the sterilizer can move smoothly on the bed cloths.

FIG. 17 is a view showing a sterilizer for bed clothes according to an embodiment of the present invention. Referring to this figure, a UV irradiating unit 250 is detachably installed to an outer surface of the housing. The UV irradiating unit 250 of an embodiment includes a switch 251 for turning on/off a UV lamp (not shown), and a power source 252 for supplying power thereto. That is, when only UV sterilization is required, the switch 251 is operated to conduct the UV sterilization in a state where the UV irradiating unit 250 is detached from the housing. Further, when the UV sterilizing and cleaning operations are required, the sterilizer can be operated in a state where the UV irradiating unit 250 is coupled to the upper surface of the housing 2100 to conduct the two operations at the same time.

FIG. 18 is a view showing a sterilizer for bed clothes according to an embodiment of the present invention. Referring to this figure, a UV irradiating unit 250 is installed in the housing to emit ultraviolet rays toward the bottom surface of the housing. Further, a hitting unit 260 for hitting a sterilizing object to allow the dust and the like adhering to the surface of the object to be detached from the surface is installed in the housing, and a brush unit 2110 is installed to the sterilizer to easily take off the foreign substances such as dust, hair or piles existing adjacent to a floor surface of a carpet from the carpet when bed clothes such as a carpet is cleaned.

The UV irradiating unit 250 is spaced apart from the floor surface by a predetermined distance by means of the ribs 211 such that the foreign substances such as dust cannot adhere to the UV irradiating unit. The brush unit 2110 includes a brush arranged in a direction perpendicular to a longitudinal direction of the sterilizer and a motor 2111 for rotating the brush. The sterilizer for bed clothes shown in FIG. 18 performs the UV sterilizing operation, the hitting operation by the hitting unit 260 and the sweeping operation by the brush, so that the efficiency of removing foreign substances such as dust using the hitting unit and brush unit and removing the harmful insects by the UV sterilization can be improved.

FIG. 19 is a view showing a sterilizer for bed clothes according to an embodiment of the present invention. Referring to this figure, the sterilizer of the previous embodiment shown in FIG. 18 is applied to a general vacuum cleaner.

That is, an additional operating unit 2310 is provided to a handle 2300 gripped by a user such that the UV irradiating unit 250, the hitting unit 260 and the brush unit 2110 can be controlled through the operating unit 2310. Further, the introduced air is purified by the first and second filter units 230 and 240, and then discharged to the outside through a hose (not shown). At this time, the second filter unit 240 may be formed similar to the first filter unit 230 such that it can be inserted in the upper portion of the housing.

FIG. 20 is a view showing a sterilizer for bed clothes according to an embodiment of the present invention. Referring to this figure, a guide 245 is further installed near the second filter unit 240 in the housing to guide air in such a manner that the air passing through a ventilation hole 244 of the second filter unit 240 is not directed to a user. When the sterilizer for bed clothes is operated, the air passing through the ventilation hole 244 of the second filter 240 is directed to a user, which may give an unpleasant feeling to the user. Thus, the guide 245 is further installed to the housing such that the air passing through the ventilation hole 245 of the second filter 240 does not flow toward the user.

FIG. 21 is a view showing a second filter unit according to an embodiment of the present invention. Referring to this figure, the second filter units 240 may be detachably installed to both sides of the sterilizer.

In the aforementioned various embodiments, a HEPA filter is used as the second filter unit, but the present invention is not limited thereto.

Embodiments of the present invention described above and illustrated in the drawings should not be construed as limiting the spirit of the invention. The scope of the present invention should be defined by only the appended claims, and the present invention can be changed or modified in various ways by those skilled in the art. Therefore, such changes and modification will be included in the scope of the present invention so long as they are apparent to those skilled in the art.

The sterilizer according to embodiments of the present invention so configured includes a sticking prevention passage extending to a bottom surface and a side surface adjacent to the bottom surface of the housing. Thus, even though the sticking prevention passage positioned at the bottom surface is closed up by a flexible cleaning object, air can be sucked up through the sticking prevention passage positioned at the side surface. Therefore, a problem in that the sterilizer cannot be easily moved forward for the sterilizing or cleaning operations due to a closed sticking prevention passage can be solved.

The sterilizer further includes a UV LED installed adjacent to the filter in addition to the UV lamp. The sterilizer also includes a heater adjacent to the discharge port. Therefore, the small harmful insects introduced into the housing of the sterilizer can be exterminated twice or three times, so that good sterilizing power against to the small harmful insects such as ticks can be obtained.

In the sterilizer, a portion where the filter unit is placed is partitioned such that only air introduced from the sticking prevention passage toward the filter unit can be sucked up but cannot be discharged. Thus, the outflow of the small harmful insects and dust can be prevented by the sterilizer. In particular, since the filter can be easily exchanged, good reliability can be provided to users.

The sterilizer includes a plurality of IR sensors installed to the bottom surface of the housing. In such a case, the sterilizer determines that there is no object approaching in front of a light emitting end, i.e. a cleaning object, if a light receiving end does not detect infrared rays emitted from the light emitting end, whereas the sterilizer determines that an object exists if the light receiving end detects the infrared rays. That is, the sterilizer is designed to stop its operation if there is no object. Thus, the convenience can be provided to the users.

The sterilizer further includes a hitting unit for hitting bed clothes such as bedding or carpet. Thus, the small harmful insects and dust adhering to the surface of the bedding or carpet can be detached from the surface by causing the bedding or carpet to be hit by the hitting unit. Further, since the detached small harmful insects and dust are sterilized (killed) and sucked up (removed), the sterilizing and cleaning efficiency can be improved.

The sterilizer includes two filtering means for purifying sucked air. Thus, the efficiency of removing or eliminating dust in the air or the small harmful insects can be improved. In particular, the second filtering means is installed to receive a portion of heat generated from the motor such that the heat from the motor can be used to sterilize the filtered small harmful insects. Therefore, the efficiency of removing harmful insects such as ticks can be improved.

Further, even though the sticking prevention passage is formed to extend to the bottom surface and the side surface adjacent to the bottom surface of the housing, bed cloths may be pushed to cover up all the sticking prevention passage. Thus, a plurality of ribs and additional caps are formed or installed to extend from the sticking prevention passage to the upper surface of the housing such that an air introduction passage can be ensured. Therefore, it is possible to solve another problem in that the sterilizer cannot be easily moved forward for the sterilizing or cleaning operations.

In addition, a means for irradiating ultraviolet rays can be detachably installed to the upper surface of the housing such that the UV irradiating means can be separately used for only the UV sterilization. Thus, there is an advantage in that a desired function can be used conveniently.

In a case where the UV irradiating means is installed in the housing, a display window is provided such that the user can confirm the operation of the UV irradiating means by the eyes of the user. Thus, it is possible to prevent any accidents caused by carelessness of the user when ultraviolet rays are irradiated. Therefore, the higher reliability of the product can be provided to the users.

Furthermore, since the UV irradiating means is spaced apart from a sterilizing object by a predetermined interval such that foreign substances such as dust cannot adhere to the UV irradiating means. Thus, the clean feeling can be always provided to the users.

Moreover, since an additional brush is further installed to clean a carpet or the like, hair or fur of pets existing on the floor of the carpet can be easily cleaned.

What is claimed is:
1. A vacuum cleaner, comprising:
   a housing comprising a bottom, a top and a side interconnecting the top and the bottom;
   at least one bottom opening formed in the bottom of the housing;
   a cavity formed in the housing in fluid communication with the at least one bottom opening;
   an ultra violet light source configured to irradiate ultra violet light to a surface under the bottom;
   a hitting duster configured to beat the surface under the bottom;
   means for forcing air in a direction within the housing to form a negative pressure in the cavity such that an air flow can be made through the at least one bottom opening from outside the housing to the cavity during operation of the vacuum cleaner;
   at least one auxiliary opening formed on at least one of the side and the top, wherein the at least one auxiliary opening is also in fluid communication with the cavity such that a substantial air flow is made through the at least one auxiliary opening from outside the housing to the cavity as a negative pressure is formed in the cavity, even if the at least one bottom opening is completely blocked during operation of the vacuum cleaner; and
   wherein the at least one auxiliary opening is provided by a plurality of ribs formed on the at least one of the side and the top of the housing.
2. The vacuum cleaner of claim 1, wherein the plurality of ribs further provide at least one air flow channel to connect to the cavity.
3. The vacuum cleaner of claim 1, wherein the top and the side of the housing do not have a discrete boundary therebetween.
4. The vacuum cleaner of claim 1, wherein the substantial air flow from the at least one auxiliary opening to the cavity is to prevent the negative pressure created in the cavity from being excessive.
5. The vacuum cleaner of claim 1, wherein the hitting duster comprises a head configured to make repeated movements to the surface and back to the housing through a hitting duster opening formed in the bottom of the housing.
6. The vacuum cleaner of claim 5, wherein the hitting duster further comprises an actuator connected to the head and configured to actuate the movements of the head.
7. The vacuum cleaner of claim 1, further comprises:
   a first filter located at a first position within the suction passage and configured to filter air flowing through the suction passage; and
   a second filter located at a second position within the suction passage downstream the first position and configured to further filter the air flowing through the suction passage past the first filter.
8. The vacuum cleaner of claim 1, further comprising a heater configured to heat air being transferred through the suction passage.
9. The vacuum cleaner of claim 1, further comprising:
   a suction passage formed in the housing and in fluid communication with the cavity so as to create a negative pressure in the cavity during operation of the vacuum cleaner, wherein the at least one bottom opening is configured to suck outside dust into the cavity when a negative pressure is created in the cavity.
10. The vacuum cleaner of claim 9, wherein the suction passage comprises an inlet open to the cavity.
11. The vacuum cleaner of claim 9, further comprising an ultra violet light source configured to irradiate ultra violet light to air being transferred through the suction passage.
12. A method of vacuum cleaning, comprising:
   providing a vacuum cleaner comprising:
      a housing comprising a bottom, a top and a side interconnecting the top and the bottom,
      at least one bottom opening formed in the bottom of the housing;
      a cavity formed in the housing in fluid communication with the at least one bottom opening,
      an ultra violet light source configured to irradiate ultra violet light to a surface under the bottom,
      a hitting duster configured to beat the surface under the bottom,
      means for forcing air in a direction within the housing to form a negative pressure in the cavity such that an air flow can be made through the at least one bottom opening from outside the housing to the cavity during operation of the vacuum cleaner, and
      at least one auxiliary opening formed on at least one of the side and the top, wherein the at least one auxiliary opening is also in fluid communication with the cavity such that a substantial air flow is made through the at least one auxiliary opening from outside the housing to the cavity as a negative pressure is formed in the cavity, even if the at least one bottom opening is completely blocked during operation of the vacuum cleaner,
      wherein the at least auxiliary opening is provided by a plurality of ribs formed on the at least one of the side and the top of the housing;
   placing the vacuum cleaner over a surface such that the bottom faces the surface to clean; and
   operating the vacuum cleaner so as to create a negative pressure in the cavity, thereby sucking dust and particles into the cavity from the surface via the at least one bottom opening, and thereby creating a substantial air flow into the cavity via the at least one auxiliary opening.

13. The method of claim 12, wherein the surface comprises a mattress surface or a bedding surface made of a fabric.

14. The method of claim 12, wherein the method further comprise irradiating ultra violet light onto the surface during the operation.

15. The method of claim 12, wherein the substantial air flow from the at least one auxiliary opening to the cavity is to prevent the negative pressure created in the cavity from being excessive.

16. The method of claim 12, wherein the housing comprises a plurality of ribs arranged so as to provide the at least one auxiliary opening.

17. The method of claim 12, wherein the vacuum cleaner further comprises a suction passage formed in the housing and in fluid communication with the cavity so as to create a negative pressure in the cavity during operation of the vacuum cleaner, wherein the at least one bottom opening is configured to suck outside dust into the cavity when a negative pressure is created in the cavity, wherein the suction passage comprises an inlet open to the cavity.

* * * * *